(12) United States Patent
Beaver et al.

(10) Patent No.: US 11,708,341 B2
(45) Date of Patent: Jul. 25, 2023

(54) SYNTHESIS OF (S)-2-AMINO-4-METHYL-((R)-2-METHYLOXIRANE-2-YL)-PENTAN-1-ONE AND PHARMACEUTICALLY ACCEPTABLE SALTS THEREOF

(71) Applicant: Amgen Inc., Thousand Oaks, CA (US)

(72) Inventors: Matthew Beaver, Natick, MA (US); Sheng Cui, Lexington, MA (US); Xiangqing Shi, Newbury Park, CA (US)

(*) Notice: Subject to any disclaimer, the term of this patent is extended or adjusted under 35 U.S.C. 154(b) by 217 days.

(21) Appl. No.: 16/327,079

(22) PCT Filed: Aug. 3, 2017

(86) PCT No.: PCT/US2017/045274
§ 371 (c)(1),
(2) Date: Feb. 21, 2019

(87) PCT Pub. No.: WO2018/027021
PCT Pub. Date: Feb. 8, 2018

(65) Prior Publication Data
US 2021/0284617 A1 Sep. 16, 2021

Related U.S. Application Data

(60) Provisional application No. 62/371,686, filed on Aug. 5, 2016, provisional application No. 62/536,862, filed on Jul. 25, 2017.

(51) Int. Cl.
*C07D 301/12* (2006.01)
*B01J 31/16* (2006.01)
*C07D 303/36* (2006.01)

(52) U.S. Cl.
CPC ........ *C07D 301/12* (2013.01); *B01J 31/1616* (2013.01); *B01J 2531/72* (2013.01); *C07D 303/36* (2013.01)

(58) Field of Classification Search
CPC .. C07D 301/12; C07D 303/36; B01J 31/1616; B01J 2531/72
USPC ........................................................ 549/523
See application file for complete search history.

(56) References Cited

U.S. PATENT DOCUMENTS

| 2005/0245435 A1 | 11/2005 | Smyth et al. |
| 2005/0256324 A1 | 11/2005 | Laidig et al. |
| 2014/0105921 A1 | 4/2014 | Phiasivongsa et al. |

FOREIGN PATENT DOCUMENTS

| CN | 104230857 A | 12/2014 |
| JP | 2010540637 | 12/2010 |
| WO | 2005121117 | 12/2005 |
| WO | 2006017842 A1 | 2/2006 |
| WO | 2006063154 A1 | 6/2006 |
| WO | 2009045497 A1 | 4/2009 |
| WO | 2010048298 A1 | 4/2010 |
| WO | 2013169282 A1 | 11/2013 |
| WO | 2014011695 A2 | 1/2014 |
| WO | 2014015016 A1 | 1/2014 |
| WO | 2014169897 A1 | 10/2014 |

OTHER PUBLICATIONS

Aldrich, 1998-1999, pp. 338, 507, 1178, 1628 (Year: 1998).*
Berge et al., "Pharmaceutical Salts," *Journal of Pharmaceutical Science*, 66(1): 1-19 (1977).
Bondzic et al., "Asymmetric Epoxidation of α-Substituted Acroleins Catalyzed by Diphenylprolinol Silyl Ether," *Organic Letters*, 12(23):5434-5437 (2010).
Hinch et al., "Effective asymmetric oxidation of enones and alkyl aryl sulfides," *Journal of Molecular Catalysis*, 251:123-128 (2006).
Lifchits et al., "The Cinchona Primary Amine-Catalyzed Asymmetric Epoxidation and Hydroperoxidation of α,β-Unsaturated Carbonyl Compounds with Hydrogen Peroxide," *Journal of the American Chemical Society*, 135:6677-6693 (2013).
Nemoto et al., "Catalytic Asymmetric Epoxidation of Enones Using La-BINOL-Triphenylarsine Oxide Complex: Structural Determination of the Asymmetric Catalyst," *Journal of the American Chemical Society*, 123:2725-2732 (2001).
Shen et al., "A Mononuclear Manganese Complex of a Tetradentate Nitrogen Ligand—Synthesis, Characterizations, and Application in the Asymmetric Epoxidation of Olefins: Bioinspired Manganese Complex for Olefin Epoxidation," *European Journal of Inorganic Chemistry*, 33:5777-5782 (2014).
Sin et al., "Total Synthesis of the Potent Proteasome Inhibitor Epoxomicin: A Useful Tool for Understanding Proteasome Biology," *Bioorganic & Medicinal Chemistry Letters*, 9:2283-2288 (1999).
Wang et al., "Manganese Catalysts with C1-Symmetric N4 Ligand for Enantioselective Epoxidation of Olefins," *Chemistry A European Journal*, 18:6750-6753 (2012).
Dunetz et al., "Large-Scale Applications of Amide Coupling Reagents for the Synthesis of Pharmaceuticals," *Organic Process Research & Development*, 20:140-177 (2016).

(Continued)

*Primary Examiner* — Taylor V Oh
(74) *Attorney, Agent, or Firm* — Amgen Inc.

(57) ABSTRACT

The present invention provides new methods for preparing compound 5, and pharmaceutically acceptable salts thereof, of structure

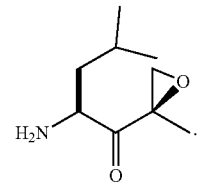

Compound 5, or a pharmaceutically acceptable salt thereof, is an important intermediate in the synthesis of carfilzomib. The invention further provides methods of making a useful manganese catalyst that may be used in the epoxidation step of the present invention.

28 Claims, No Drawings

(56) References Cited

OTHER PUBLICATIONS

Zhang et al., "Design, Synthesis and Biological Evaluation of Peptidyl Epoxyketone Proteasome Inhibitors Composed of β-amino Acids," *Chemical Biology & Drug Design,* 84(5): 497-504 (2014).
Shibata et al., "Asymetric Transformation of Alanine via Optically Labile Imidazolines", Bull. Chem. Soc. 52(10):2938-41 (1979).

* cited by examiner

SYNTHESIS OF (S)-2-AMINO-4-METHYL-((R)-2-METHYLOXIRANE-2-YL)-PENTAN-1-ONE AND PHARMACEUTICALLY ACCEPTABLE SALTS THEREOF

RELATED APPLICATIONS

This application is a national phase of International patent application PCT/US2017/045274 filed on Aug. 3, 2017 which claims the benefit of U.S. Provisional patent application 62/371,686 filed on Aug. 5, 2016 and the benefit of U.S. Provisional patent application 62/536,862 filed on Jul. 25, 2017, all of which are hereby incorporated herein by reference in their entireties for all purposes.

FIELD OF THE INVENTION

The present invention relates to an improved, efficient, scalable process to prepare an intermediate, (S)-2-amino-4-methyl-1-((R)-2-methyloxirane-2-yl)pentan-1-one, useful for the synthesis of carfilzomib.

BACKGROUND OF THE INVENTION

Carfilzomib, also known as Kyprolis®, is a tetrapeptide epoxy ketone proteosome inhibitor that binds selectively and irreversibly to the constitutive proteosome and immunoproteosome. More specifically, the electrophilic epoxyketone warhead binds to the catalytic threonine residue of the β5 subunit of the proteasome protein. Carfilzomib is approved for human use, for the treatment of multiple myeloma. Carfilzomib and various methods of making carfilzomib are described in US patent publications US20050245435, US20140105921 and in PCT published patent applications WO2006017842, WO2009045497, WO2014169897, WO2013169282, WO2014011695, WO2006063154, WO2014015016, and WO2010048298, each specification of which is hereby incorporated herein by reference in its entirety.

One intermediate that may be used in the synthesis of carfilzomib is a compound 5, or a pharmaceutically acceptable salt thereof where X− is present, of the formula:

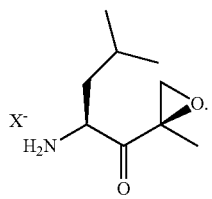

5

Compound 5 having a chemical name of (S)-2-amino-4-methyl-1-((R)-(2-methyloxirane-2-yl)pentan-1-one (as named by ChemBioDraw Ultra software, version 12.0). Sin and colleagues at Yale used this intermediate in the synthesis of epoxomicin (N. Sin et al., *Bioorg. Med Chem. Letters*, 9 2283-2288, 1999). They synthesized this intermediate beginning with Boc-leucine-weinreb amide 9 and proceeded through a multi-step synthesis generating the corresponding α,β-unsaturated ketone 10, and finally epoxidation of the double bond using hydrogen peroxide as the oxidant to afford a mixture of 11a and 11b in a 1.7:1 ratio, as shown schematically below (also see Sin, page 2285, scheme 1).

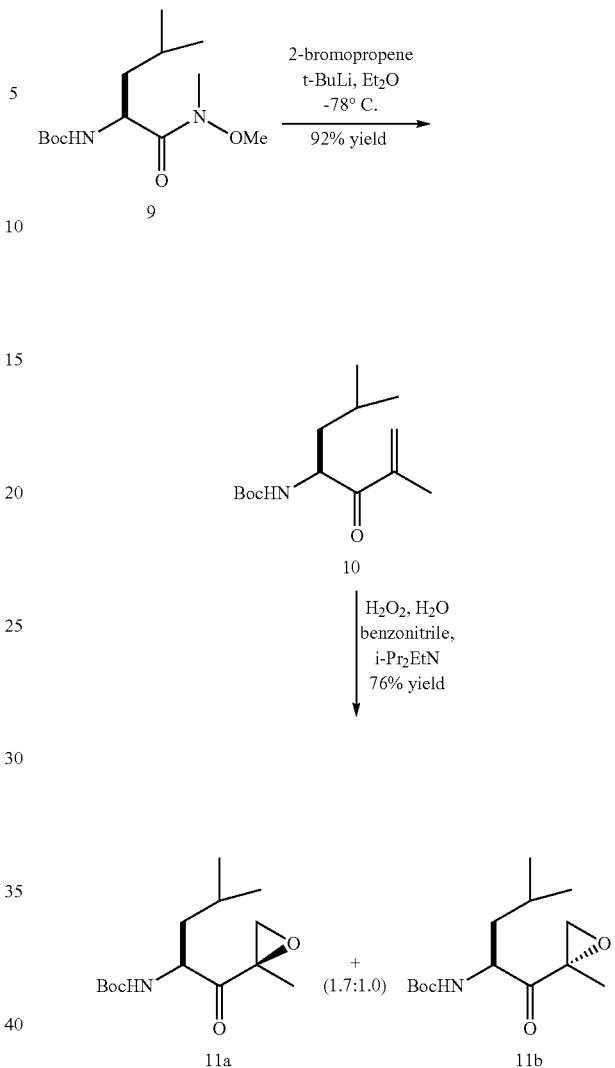

The compounds 11a and 11b can be separated by column chromatography, and the Boc protecting group of compound 11a is removed with acid, such as trifluoroacetic acid (TFA), to provide the desired epoxide intermediate (S)-2-amino-4-methyl-1-((R)-2-methyloxirane-2-yl)pentan-1-one as a TFA salt.

Patent publication WO2009045497 describes the synthesis of Boc or other amino-protected epoxyketone intermediate 11a (Boc protected amine shown above) using aqueous calcium hypochlorite or aqueous sodium hypochlorite (bleach), as the oxidizing agent, in the presence of a co-solvent such as pyridine, acetonitrile, DMF, DMSO, N-methylpyrrolidinone (NMP), DMA, THF and nitromethane, to convert compound 10 (above) to a 1:1 mixture of product 11a and 11b.

US patent publication US20050256324 describes the synthesis of amino acid epoxyketones, and particularly the synthesis of intermediate 5. This publication teaches that intermediate 5 may be prepared from the carboxybenzyl (cbz) protected amino-α,β-unsaturated ketone 20 (see scheme below) to the corresponding carboxybenzyl protected amino epoxyketone 23a, as illustrated:

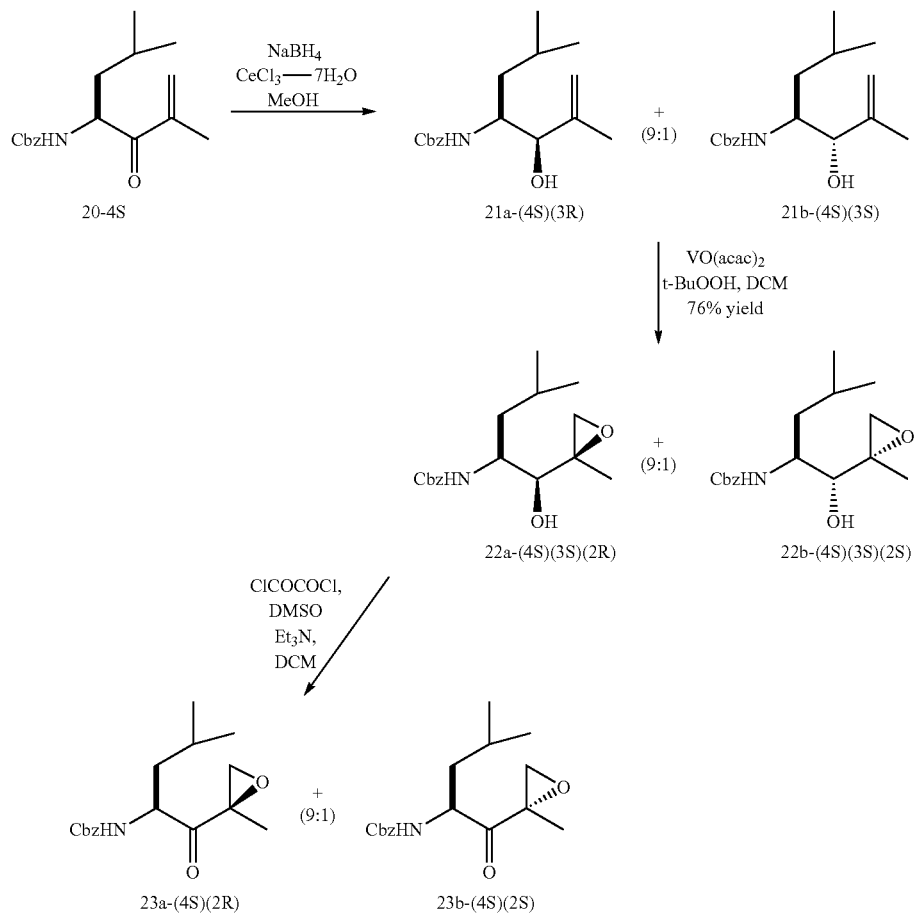

Compounds 23a and 23b can be separated from the mixture using column chromatography (assumes the 9:1 mixture of 21a:21b was carried through without separation), and the amine protecting carboxybenzyl group of compound 23a is removed using known, conventional methods such as hydrogenation with a suitable metal catalyst, such as palladium on carbon, to provide the desired epoxide intermediate (S)-2-amino-4-methyl-1-((R)-2-methyloxirane-2-yl)pentan-1-one (23a) as a free base.

US patent publication US20050256324 also discloses a process where intermediate 23a may alternatively be prepared using metachloroperbenzoic acid (mCPBA) in dichloromethane (DCM), or Dess-Martin Periodinane in dimethylsulfoxide (DMSO) or tetrapropylammonium perruthenate (TPAP) with 4-methylmorpholine-N-Oxide (NMO) in DCM, as the oxidizing agents, respectively. The mCPBA method was described to replace the previously taught VO(acac)$_2$ oxidizing agent (shown above) with these as agents.

A more recent publication (Wang, B et al, *Chemistry European Journal*, 18, 6750-6753, 2012) discloses the use of a manganese catalyst to enantioselectively convert an olefin to an epoxide. It further mentions the application of this technique to preparing the epoxide intermediates of epoxomicin and of carfilzomib. More specifically, starting with Boc-L-Leu-OH, this reference teaches that the corresponding epoxyketone intermediate may be prepared in a 7:1 diastereomeric ratio in favor of the undesired (S,S) epoxide intermediate diastereomer using hydrogen peroxide as the oxidizing agent (see Wang scheme 2).

While these procedures to prepare intermediate compound 5 are methods that afford intermediate 5 (shown above), they are not very practical, not very efficient from a time, effort and cost perspective, and not very effective. Thus, these methods are not optimal for the manufacture of intermediate 5 for the global manufacture and sale of the commercial drug product carfilzomib. For instance, the process taught in Sin utilizes highly pyrophoric reagents (t-BuLi) and cryogenic reaction conditions (−78° C.) and results in a less than optimal overall yield of intermediate 11a. The final epoxidation step provides an overall 76% product yield containing a mixture of diastereomers (1.7:1) thus requiring time consuming, and costly column chromatographic separation to isolate the desired product. On a large manufacturing scale, such column chromatography will generate huge solvent waste which is environmentally unfriendly. Thus, the undesired and unusable 35-40% reaction product with the wrong, undesired stereochmistry from the method taugh in Sin increases overall costs and contributes chemical waste that adds disposal expense and potential harm to the environment.

The process taught in US20050256324 consists of more steps than those taught in Sin and utilizes expensive reagents. This process goes through the additional step of reducing the ketone using environmentally unfriendly and costly borane and cerium catalysts to provide the corresponding alcohol. Despite the 9:1 ratio of the desired diastereomer 22a to the undesired diastereomer 22b, one must then perform another reaction to oxidize the hydroxyl group of the diastereomeric mixture up to the corresponding ketone. This process effectively reduces the ketone then re-oxidizes the same ketone. Thus, while the diastereoselectivity may be improved relative to Sin, this process is synthetically inefficient thereby increasing associated costs, time, waste generation and labor of production.

The process taught in WO2009045497 utilized bleach to accomplish the epoxidation reaction avoiding the inefficient reduction/oxidation cycle of the adjacent ketone. However, this epoxidation reaction results in about a 1:1 ratio of (R) and the (S) stereoisomers at the epoxide carbon. In addition, the oxidation reaction with bleach is an exothermic reaction to the extent of being a potential safety hazard, particularly when conducted on a larger, manufacturing scale. To this end, this process requires costly and time-consuming chromatographic separation and re-crystallizations to isolate the desired stereoisomeric product, resulting in significant waste.

The process taught in Wang provides diastereoselective epoxidation reaction favoring the undesired epoxide stereochemistry. The desired epoxide diastereomer only accounts for 12% of the crude reaction mixture. Therefore, use of this process is overall low yielding, and would require a laborious column chromatography step resulting in increased time and expense, as well as to the potential of having to dispose of additional chemical waste. To this end, the literature teaches epoxidation processes that are simply not very efficient and/or sub-optimal for large scale production of the commercial drug product carfilzomib. Therefore, there is a need to identify alternative synthetic methods, of increased efficiency and effectiveness, to prepare key intermediate 5 for the manufacture of carfilzomib.

BRIEF DESCRIPTION OF THE INVENTION

The present invention provides a new method for the synthesis of keto-epoxide intermediate compound 5

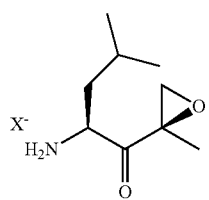

or a pharmaceutically acceptable salt thereof where $X^-$ is present, the method comprising steps 1-5 according to scheme 1

Scheme I

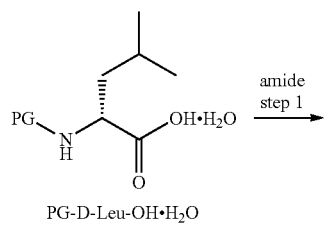

PG-D-Leu-OH·H$_2$O

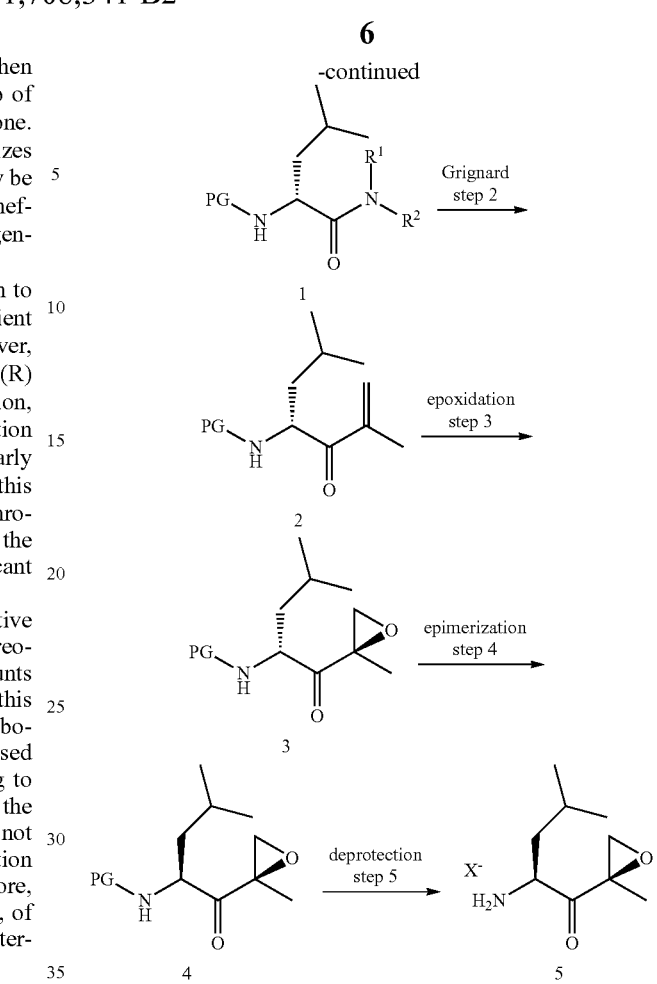

wherein
PG is a protecting group selected from t-butoxycarbonyl (Boc) and carboxybenzyl (cbz);
$R^1$ is $CH_3$ and $R^2$ is —$OCH_3$ or $R^1$ and $R^2$ taken together with the nitrogen atom to which they are attached form a morpholine ring;
$X^-$ is absent or $X^-$ is an addition salt anion selected from TFA, Cl, Br, I and mesylate;
the amide step 1 comprises use of an acid activating agent and a basic amine selected from ($CH_3$)NH($OCH_3$) and morpholine;
the Grignard step 2 comprises use of isopropyl magnesiumchloride, Mg and 2-bromopropene or isopropenylmagnesium bromide;
the epoxidation step 3 comprises use of an oxidizing agent and a manganese catalyst;
the epimerization step 4 comprises the use of a base; and
the deprotection step 5 comprises use of a catalyst or an acid.

The invention further provides various reaction conditions and reagents that may be used to prepare compound 5, as discussed further herein. The method of the present invention is efficient from a bond construction perspective. For example, it involves an amine protected α,β-unsaturated ketone compound 2 and converts the double bond directly to the corresponding epoxide group with a strong preference for the desired 2R epoxide isomer, such as that shown in compound 3 (above). The process is advantageously diastereoselective in its epoxidation step 3. The method results in high overall yields of compound 5 and enables the process to be scaled up to large, manufacturing grade scales. The present invention provides fewer synthetic steps, requires no column chromatography to separate diastereomeric mixtures and/or produces less chemical and environmentally harmful waste materials than the various different methods taught in the art. To this end, the present invention results in surprising and unexpected advantages including, without limitation, reduced time, reduced expense, and reduced waste, when compared to those methods for making the keto-epoxide intermediate compound 5 described in the art.

DETAILED DESCRIPTION OF THE INVENTION

The present invention provides novel methods of preparing a keto-epoxide intermediate compound 5, as either a free base or a pharmaceutically acceptable salt thereof, for the synthesis of carfilzomib.

The terms "aspect" and "embodiment" are used interchangeably herein.

In aspect 1 of the invention, the invention provides a method of making compound 5

5

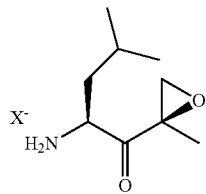

or a pharmaceutically acceptable salt thereof where X⁻ is present, the method comprising steps 1-5 according to scheme 1

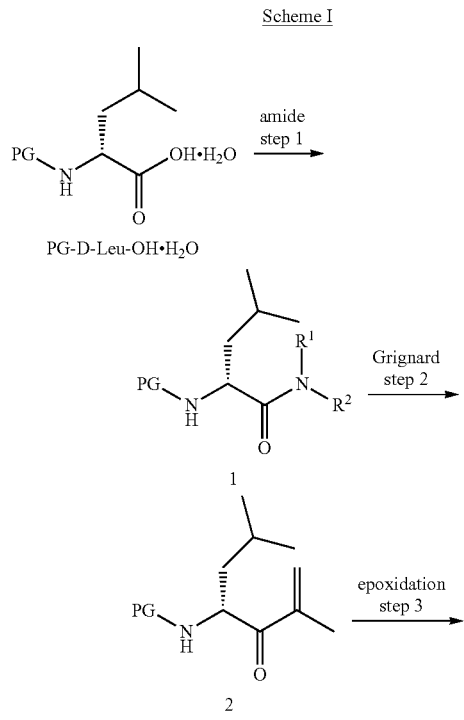

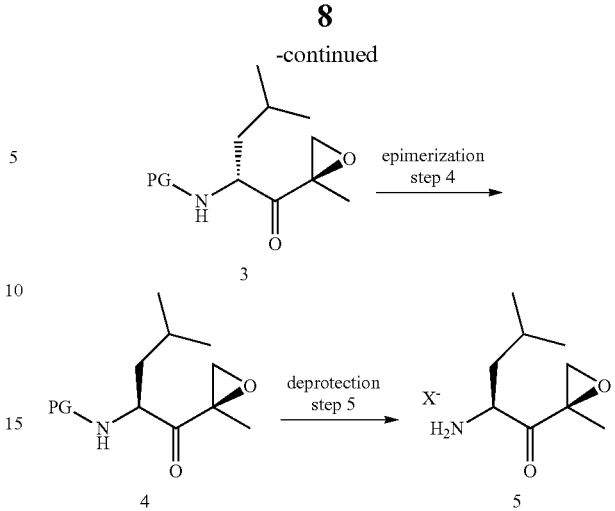

wherein
PG is a protecting group selected from t-butoxycarbonyl and carboxybenzyl;
$R^1$ is $CH_3$ and $R^2$ is —$OCH_3$ or $R^1$ and $R^2$ taken together with the nitrogen atom to which they are attached form a morpholine ring;
$X^-$ is absent or $X^-$ is an addition salt anion selected from TFA, Cl, Br, I and mesylate;
the amide step 1 comprises use of an acid activating agent and a basic amine selected from $(CH_3)NH(OCH_3)$ and morpholine;
the Grignard step 2 comprises use of isopropyl magnesiumchloride, Mg and 2-bromopropene or isopropenylmagnesium bromide;
the epoxidation step 3 comprises use of an oxidizing agent and a manganese catalyst;
the epimerization step 4 comprises the use of a base; and
the deprotection step 5 comprises use of a catalyst or an acid.

In aspect 2 of the invention, the invention provides the method of aspect 1 wherein PG is Boc.

In aspect 3 of the invention, the invention provides the method of aspect 1 wherein PG is carboxybenzyl.

In aspect 4, the invention provides product compound 1 of the amide step 1 wherein $R^1$ is $CH_3$ and $R^2$ is —$OCH_3$.

In aspect 4a, the invention provides product compound 1 of the amide step 1 wherein $R^1$ and $R^2$ taken together with the nitrogen atom to which they are attached form a morpholine ring.

In aspect 5 of the invention, the invention provides the method of any one of aspects 1, 2, 3, 4 and 4a wherein the amide step 1 comprises the use of an acid activating agent.

In aspect 5a of the invention, the invention provides the method of any one of aspects 1, 2, 3, 4 and 4a wherein the acid activating agent used in the amide step 1 is an acid chloride, an anhydride, a carbodiimide, a CDI, a phosphonium salt or a guanidinium or uranium salt.

In aspect 5b of the invention, the invention provides the method of aspects 5a and 4b wherein acid activating agent is a carbodiimide selected from DCC, DIC and EDC.

In aspect 5c of the invention, the invention provides the method of aspects 5a and 4b wherein acid activating agent is a pohosphonium salt selected from BOP and PyBOP.

In aspect 5d of the invention, the invention provides the method of aspects 5a and 4b wherein acid activating agent is (a) an acid chloride made using an agent selected from thionyl chloride, oxalyl chloride and phosphorus oxychloride; or (b) an anhydride using an agent selected from ethylchloroformate (ECF), isobutylchloroformate (IBCF), boc anhydride, EEDQ, acetic anhydride and pivaloyl chloride.

In aspect 5e of the invention, the invention provides the method of any one of aspects 1, 2, 3, 4 and 4a wherein the acid activating agent used in the amide step 1 is CDI.

In aspect 5f of the invention, the invention provides the method of any one of aspects 1, 2, 3, 4, 4a and 5 wherein the acid activating agent used in the amide step 1 is CDI and the amide step 1 reaction is conducted at a temperature of at or below 20° C.

In aspect 5f-1 of the invention, the invention provides the method of any one of aspects 1, 2, 3, 4, 4a and 5 wherein the acid activating agent used in the amide step 1 is CDI and the amide step 1 reaction is conducted at a temperature of at or below 10° C.

In aspect 5g of the invention, the invention provides the method of any one of aspects 1, 2, 3, 4, 4a, 5e and 5f wherein the acid activating agent used in the amide step 1 is CDI and wherein the CDI is added at a temperature of 5° C. or less and the morpholine is added at a temperature of 10° C. or less.

In aspect 6 of the invention, the invention provides the method of any one of aspects 1-4, 4a, 5 and 5a-5g wherein the Grignard step 2 comprises use of isopropyl magnesiumchloride, Mg and 2-bromopropene.

In aspect 6a of the invention, the invention provides the method of any one of aspects 1-4, 4a, 5 and 5a-5g wherein the Grignard step 2 comprises use of isopropenylmagnesium bromide.

In aspect 7 of the invention, the invention provides the method of any one of aspects 1-4, 4a, 5, 5a-5g and 6 wherein the oxidizing agent used in the epoxidation step 3 is hydrogen peroxide, peracetic acid, t-BuOOH and PhIO.

In aspect 7a of the invention, the invention provides the method of any one of aspects 1-4, 4a, 5, 5a-5g and 6 wherein the oxidizing agent used in the epoxidation step 3 is hydrogen peroxide.

In aspect 7b of the invention, the invention provides the method of any one of aspects 1-4, 4a, 5, 5a-5g and 6 wherein the oxidizing agent used in the epoxidation step 3 is t-BuOOH and PhIO.

In aspect 8 of the invention, the invention provides the method of any one of aspects 1-4, 4a, 5, 5a-5g, 6, 6a, 7 and 7a-7b wherein manganese catalyst used in the epoxidation step 3 has a structure of

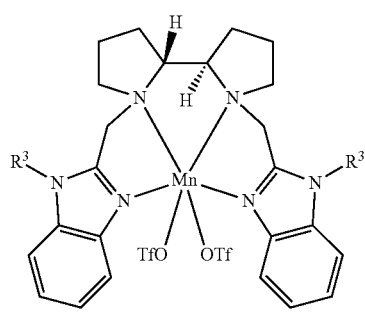

wherein each $R^3$, independently, is $C_{1-6}$alkyl.

In aspect 8a, the invention provides a method of aspect 8 wherein each $R^3$, independently, is methyl or ethyl.

In aspect 8b of the invention, the invention provides the method of any one of aspects 1-4, 4a, 5, 5a-5g, 6, 6a, 7 and 7a-7b wherein manganese catalyst used in the epoxidation step 3 has a structure of

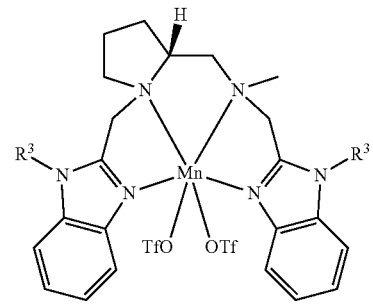

wherein each $R^3$, independently, is methyl or ethyl.

In aspect 8c of the invention, the invention provides the method of any one of aspects 1-4, 4a, 5, 5a-5g, 6, 6a, 7 and 7a-7b wherein manganese catalyst used in the epoxidation step 3 has a structure of

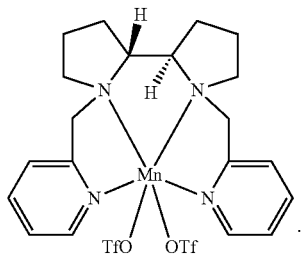

In aspect 9 of the invention, the invention provides the method of any one of aspects 1-4, 4a, 5, 5a-5g, 6, 6a, 7, 7a-7b and 8 wherein manganese catalyst used in the epoxidation step 3 has a structure of

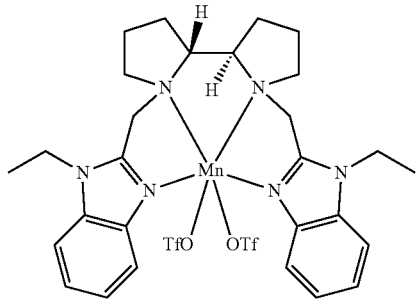

In aspect 10 of the invention, the invention provides the method of any one of aspects 1-4, 4a, 5, 5a-5g, 6, 6a, 7, 7a-7b, 8, 8a-8c and 9 wherein the base used in the epimerization step 4 is selected from DBU, triazabicyclodecene (TBD), pyrrolidine, potassium carbonate and sodium hydroxide.

In aspect 11 of the invention, the invention provides the method of any one of aspects 1-4, 4a, 5, 5a-5g, 6, 6a, 7, 7a-7b, 8, 8a-8c, 9 and 10 wherein the base used in the epimerization step is DBU.

In aspect 11a of the invention, the invention provides the method of any one of aspects 1-4, 4a, 5, 5a-5g, 6, 6a, 7, 7a-7b, 8, 8a-8c, 9 and 10 wherein the base used in the epimerization step is TBD.

In aspect 11b of the invention, the invention provides the method of any one of aspects 1-4, 4a, 5, 5a-5g, 6, 6a, 7, 7a-7b, 8, 8a-8c, 9 and 10 wherein the base used in the epimerization step is TBD in an amount ranging from about 0.01 to about 0.1 equivalents.

In aspect 12 of the invention, the invention provides the method of any one of aspects 1-4, 4a, 5, 5a-5g, 6, 6a, 7, 7a-7b, 8, 8a-8c, 9, 10 and 11 further comprising a solvent swap involving a switch to an alcohol solvent or a basic solvent.

In aspect 13 of the invention, the invention provides the method of any one of aspects 1-4, 4a, 5, 5a-5g, 6, 6a, 7, 7a-7b, 8, 8a-8c, 9, 10 and 11 further comprising a solvent swap involving a switch to methanol, isopropanol or N-methylpyrrolidinone.

In aspect 13a of the invention, the invention provides the method of any one of aspects 1-4, 4a, 5, 5a-5g, 6, 6a, 7, 7a-7b, 8, 8a-8c, 9, 10 and 11 further comprising a solvent swap involving a switch to methanol.

In aspect 14a, the invention provides a method of making compound 4a

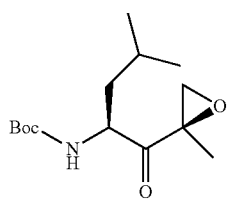

4a the method comprising steps 1-4 according to scheme 1-a

Scheme 1-a

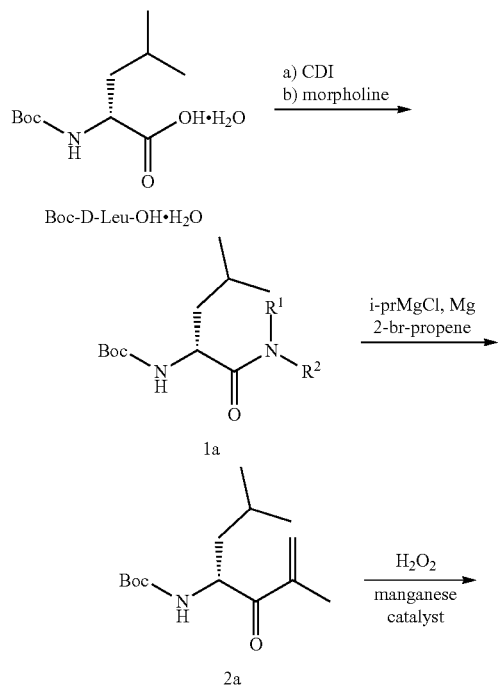

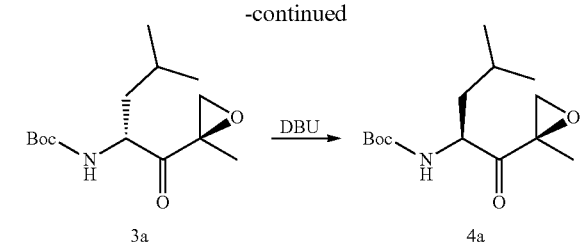

wherein $R^1$ is $CH_3$ and $R^2$ is —$OCH_3$ or $R^1$ and $R^2$ taken together with the nitrogen atom to which they are attached form a morpholine ring, and manganese catalyst has a structure of

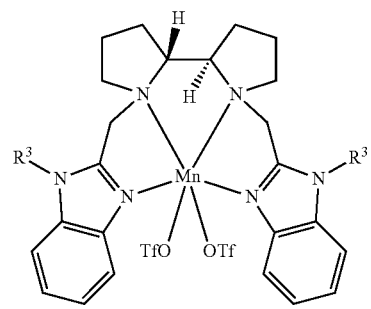

wherein each $R^3$, independently, is methyl or ethyl.

In aspect 14a, the invention provides a method of making compound 4a

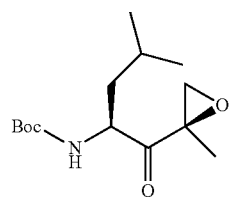

4a the method comprising steps 1-4 according to scheme 1-a

Scheme 1-a

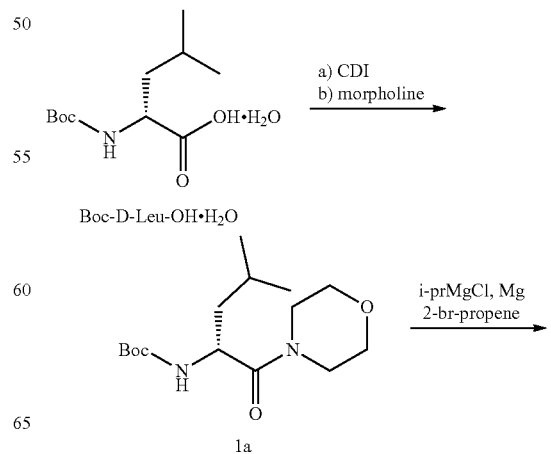

-continued

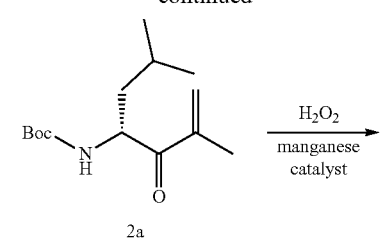
2a

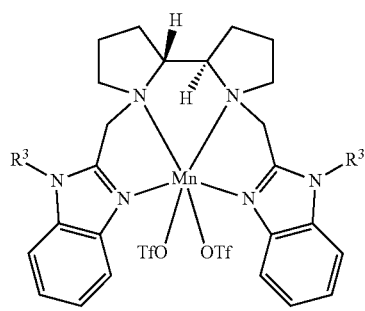
3a  4a wherein the manganese catalyst has a structure of

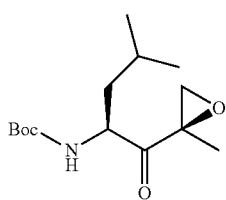

wherein each $R^3$, independently, is methyl or ethyl.

In aspect 14b, the invention provides a method of making compound 4a

4a

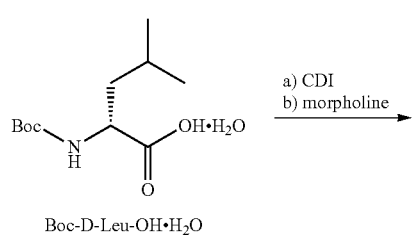

the method comprising steps 1-4 according to scheme 1-a

Scheme 1-a

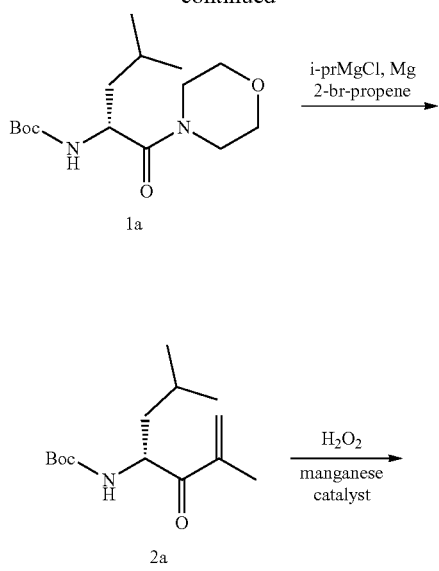
1a

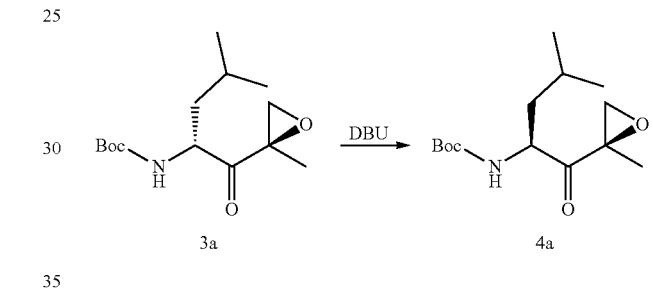
3a  4a wherein

CDI is used in an amount ranging from about 1.0 equivalents to about 2.5 equivalents;

morpholine is used in an amount ranging from about 1.2 equivalents to about 2.0 equivalents;

2-bromopropene is used in an amount ranging from about 1.5 equivalents to about 3.5 equivalents;

hydrogen peroxide is used in an amount ranging from about 1.5 equivalents to about 3.0 equivalents;

the manganese catalyst has a structure of

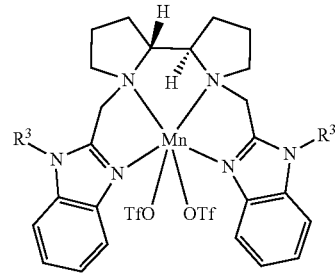

wherein each $R^3$, independently, is methyl or ethyl, and used in an amount ranging from about 0.0002 equivalents to about 0.001 equivalents; and DBU is used in an amount ranging from about 0.1 to about 0.5 equivalents.

In aspect 14c, the invention provides a method of making compound 4a

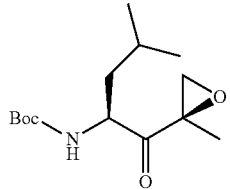

the method comprising steps 1-4 according to scheme 1-a

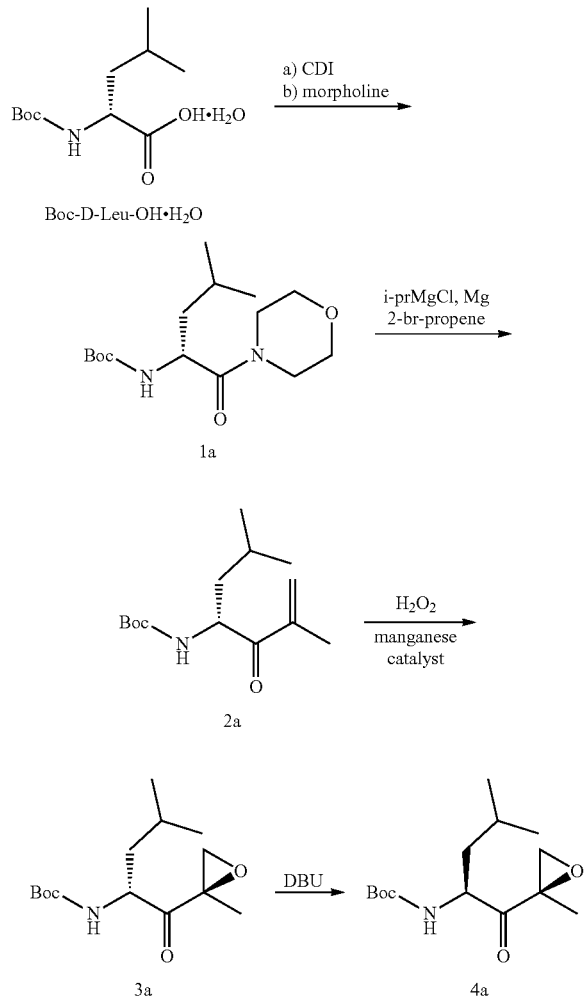

wherein

CDI is used in an amount of about 2.0 equivalents;

morpholine is used in an amount of about 1.5 equivalents;

2-bromopropene is used in an amount of about 3.0 equivalents;

hydrogen peroxide is used in an amount of about 2.0 equivalents;

the manganese catalyst has a structure of

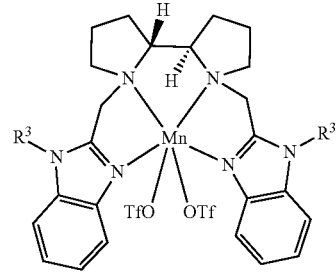

wherein each $R^3$, independently, is ethyl, and used in an amount of about 0.001 equivalents; and TBD is used in an amount of about 0.1 equivalents.

In aspect 15 of the invention, the invention provides the method of any one of aspects 14 and 14a wherein manganese catalyst has a structure of

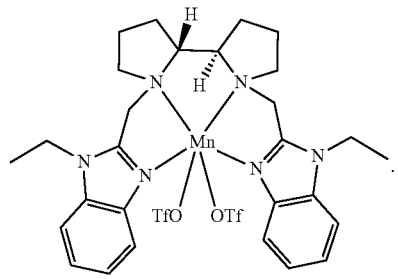

In aspect 15a of the invention, the invention provides the method of any one of aspects 14, 14a and 15 wherein manganese catalyst used in the epoxidation step 3 has a structure of

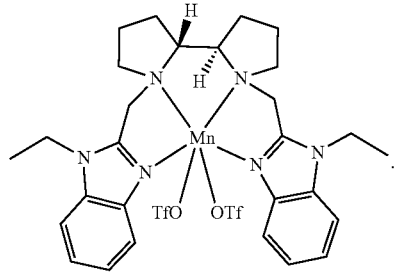

In aspect 16 of the invention, the invention provides the method of any one of aspects 1-4, 4a, 5, 5a-5g, 6, 6a, 7, 7a-7b, 8, 8a-8c, 9, 10, 11, 12, 13, 14, 14a, 15 and 15a wherein the manganese catalyst is used in a amount ranging from about 0.0001 to about 0.002 molar equivalents to the moles of the starting material compound 2a.

In aspect 16a of the invention, the invention provides the method of any one of aspects 1-4, 4a, 5, 5a-5g, 6, 6a, 7, 7a-7b, 8, 8a-8c, 9, 10, 11, 12, 13, 14, 14a, 15 and 15a wherein the manganese catalyst is used in a amount ranging from about 0.0002 to about 0.0006 molar equivalents to the moles of the starting material compound 2a.

In aspect 17 of the invention, the invention provides the method of any one of aspects 1-4, 4a, 5, 5a-5g, 6, 6a, 7, 7a-7b, 8, 8a-8c, 9, 10, 11, 12, 13, 14, 14a, 15, 15a, 16 and 16a wherein the manganese catalyst is used in an amount of about 0.0004 molar equivalents to the moles of the starting material 2 or 2a.

In aspect 17a of the invention, the invention provides the method of any one of aspects 1-4, 4a, 5, 5a-5g, 6, 6a, 7, 7a-7b, 8, 8a-8c, 9, 10, 11, 12, 13, 14, 14a, 15, 15a, 16 and 16a wherein the manganese catalyst is used in an amount of about 0.001 molar equivalents to the moles of the starting material 2 or 2a.

In aspect 18 of the invention, the invention provides the method of any one of aspects 12-13 and 17 wherein the solvent swap comprises a switch from ACN to isopropanol between the Grignard step and the epoxidation step.

In aspect 19 of the invention, the invention provides the method of any one of aspects 1-4, 4a, 5, 5a-5g, 6, 6a, 7, 7a-7b, 8, 8a-8c, 9, 10, 11, 14, 14a-14c, 15, 15a and 16-18 further comprising a solvent swap involving a switch to methanol, isopropanol or N-methylpyrrolidinone.

In aspect 19a of the invention, the invention provides the method of any one of aspects 1-4, 4a, 5, 5a-5g, 6, 6a, 7, 7a-7b, 8, 8a-8c, 9, 10, 11, 14, 14a-14c, 15, 15a and 16-18 further comprising a solvent swap involving a switch to methanol.

In aspect 20, the invention provides a compound of structure 5

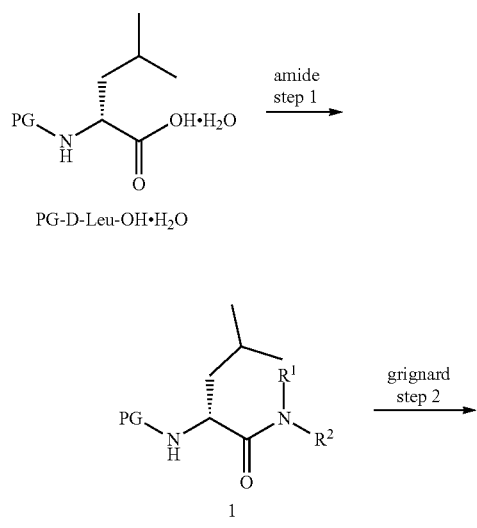

or a pharmaceutically acceptable salt thereof where X⁻ is present, prepared by the process according to scheme 1

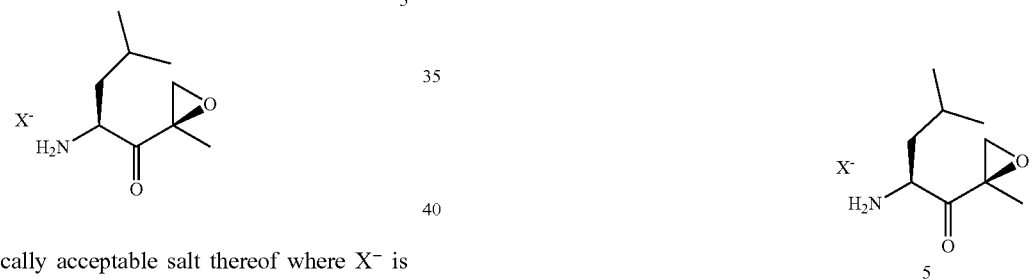

wherein

PG is a protecting group selected from t-butoxycarbonyl and carboxybenzyl;

$R^1$ is $CH_3$ and $R^2$ is $-OCH_3$ or $R^1$ and $R^2$ taken together with the nitrogen atom to which they are attached form a morpholine ring;

$X^-$ is absent or $X^-$ is an addition salt anion selected from TFA, Cl, Br, I and mesylate;

the amide step 1 comprises use of an acid activating agent selected from CDI, DCC, TBTU, HATU, PyBOP, TCTU, EDCI, pivaloyl chloride, isobutylchloroformate, propylphosphonic anhydride and N,N-diisopropylcarbodiimide (DIC) and a basic amine selected from $(CH_3)NH(OCH_3)$ and morpholine;

the Grignard step 2 comprises use of isopropyl magnesiumchloride, Mg and 2-bromopropene or isopropenylmagnesium bromide;

the epoxidation step 3 comprises use of an oxidizing agent and a manganese catalyst wherein the manganese catalyst has a structure of

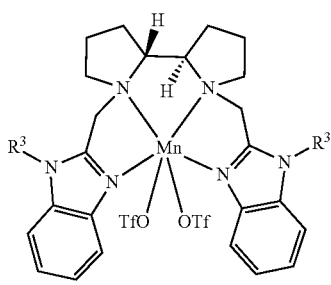

wherein each R³, independently, is methyl or ethyl;

the epimerization step 4 comprises the use of a base; and the deprotection step 5 comprises use of a catalyst or an acid.

In aspect 20a of the invention, the invention provides the method of aspect 20 wherein manganese catalyst has a structure of

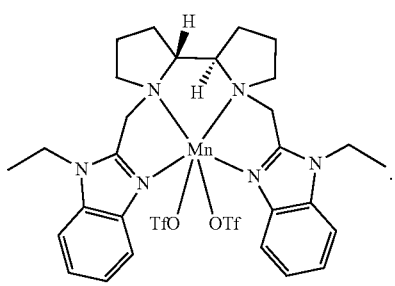

In aspect 21, the invention provides a compound 4a

4a

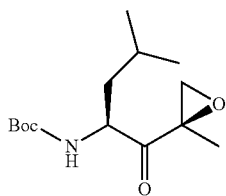

prepared by the process according to scheme 1-a

Scheme 1-a

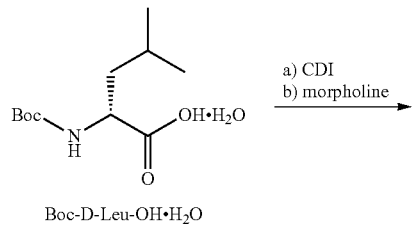

Boc-D-Leu-OH·H₂O

-continued

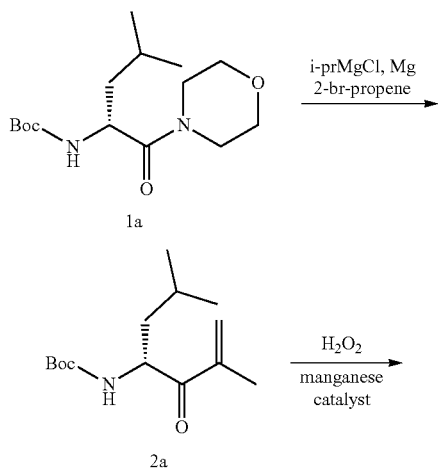

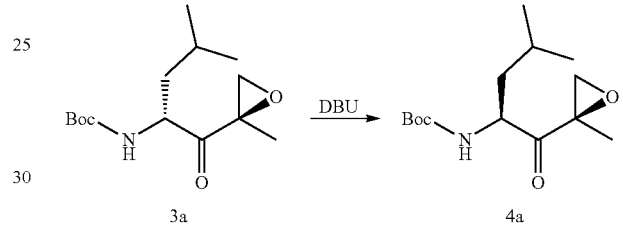

wherein the manganese catalyst has a structure of

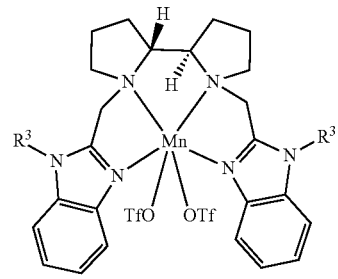

wherein each R³, independently, is methyl or ethyl.

In aspect 21a of the invention, the invention provides the method of aspect 21 wherein manganese catalyst has a structure of

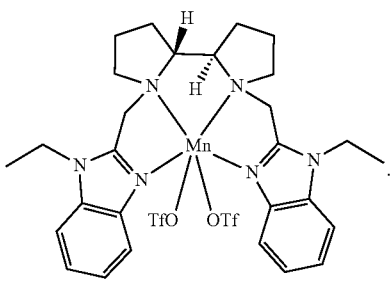

21

In aspect 21b, the invention provides compound 4a

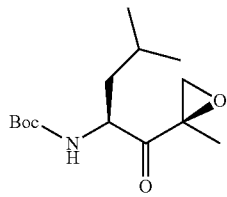

prepared by the process according to scheme 1-a

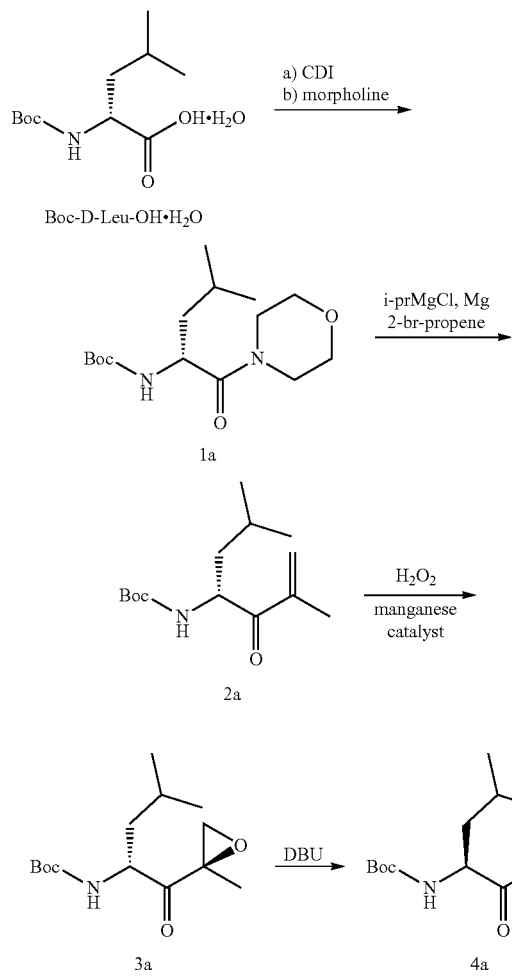

wherein

CDI is used in an amount ranging from about 1.0 equivalents to about 2.5 equivalents;

morpholine is used in an amount ranging from about 1.2 equivalents to about 2.0 equivalents;

2-bromopropene is used in an amount ranging from about 1.5 equivalents to about 3.5 equivalents;

hydrogen peroxide is used in an amount ranging from about 1.5 equivalents to about 3.0 equivalents;

22 the manganese catalyst has a structure of

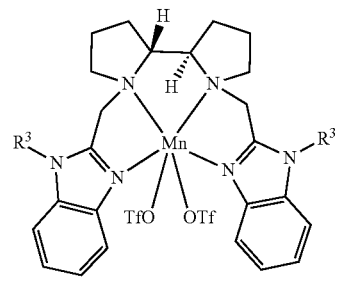

wherein each $R^3$, independently, is methyl or ethyl, and used in an amount ranging from about 0.0002 equivalents to about 0.001 equivalents; and TBD is used in an amount ranging from about 0.01 to about 0.1 equivalents.

In aspect 21c, the invention provides compound 4a

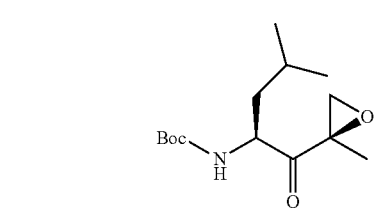

prepared by the process according to scheme 1-a

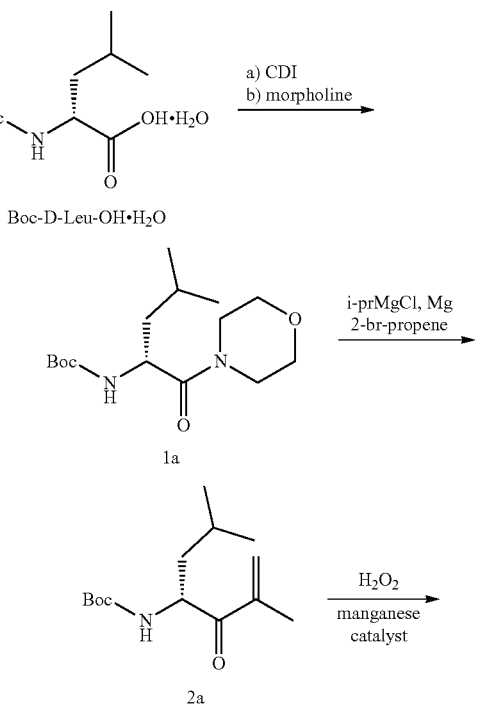

-continued

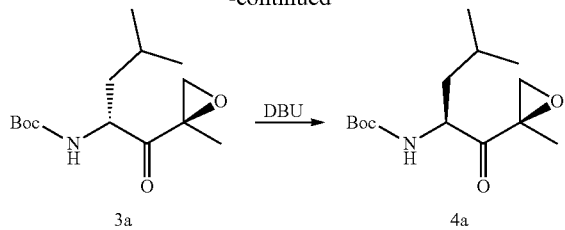

wherein
CDI is used in an amount of about 2.0 equivalents;
morpholine is used in an amount of about 1.5 equivalents;
2-bromopropene is used in an amount of about 3.0 equivalents;
hydrogen peroxide is used in an amount of about 2.0 equivalents;
the manganese catalyst has a structure of

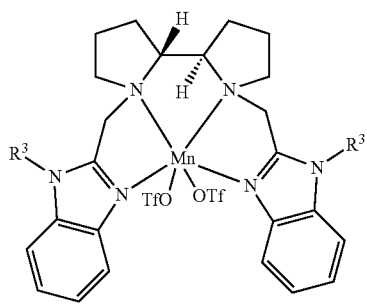

wherein each $R^3$, independently, is ethyl, and used in an amount of about 0.001 molar equivalents; and
TBD is used in an amount of about 0.1 equivalents.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned in the brief description of the invention and later sections herein are incorporated by reference herein in their entirety. In case of conflict, the present specification, including definitions, will control. Other features and advantages of the disclosure will be apparent from the following additional description, examples and from the claims set forth hereinbelow.

Definitions

The following definitions should further assist in understanding the terms as used herein and the scope of the invention described herein.

The term "$C_{x-y}$alkyl" refers to substituted or unsubstituted saturated hydrocarbon groups, including straight-chain alkyl and branched-chain alkyl groups that contain from x to y carbons in the chain. The term "haloalkyl" refers to alkyl groups in which at least one hydrogen atom is replace by a halo (e.g., fluoro, chloro, bromo, iodo), e.g., $CH_2F$, $CHF_2$, trifluoromethyl and 2,2,2-trifluoroethyl.

The term "comprising" is meant to be open ended, including the indicated component(s) but not excluding other elements.

The term "equivalents' is intended to mean molar equivalents, as commonly understood by persons of ordinary skill in the art.

The term "pharmaceutically acceptable salt" refers to the relatively non-toxic, inorganic and organic acid addition salts of the compound 5 of the invention. The nature of the salt is not critical, provided that it is pharmaceutically-acceptable. These salts can be prepared in situ during the final isolation and purification of the compound(s), or by separately reacting a purified compound in its free base form with a suitable organic or inorganic acid, and isolating the salt thus formed. Suitable pharmaceutically-acceptable acid addition salts of the compound may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid (See, for example, Berge et al. (1977) "Pharmaceutical Salts", J. Pharm. Sci. 66: 1-19.).

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate and if allowed by valence.

General Synthesis and Representative Examples of the Invention

The following abbreviations used throughout the description, including the general schemes and the examples, mean the following:

ACN acetonitrile
Boc t-butoxycarbonyl
cbz carboxybenzyl
CDI carbonyldiimidazole (acid activating agent)
DBU 1,8-diazabicyclo[5.4.0]undec-7-ene
DCM dichloromethane; methylene dichloride
DMF dimethylformamide
DMSO dimethyl sulfoxide
eq, equiv equivalent (molar)
EtOAc ethyl acetate
g. gm gram
HOAc acetic acid
IPAc ispropyl acetate
MeOH methanol
mL, ml milliliter
Mg magnesium
Mn manganese
mpk, mg/kg milligram per kilogram
RT, rt room temperature
NaCl sodium chloride
NaOH sodium hydroxide
tBuOH t-butanol; t-butyl alcohol
THF tetrahydrofuran Representative Examples of the Invention The following carfilzomib prodrug compounds are representative examples of the invention and are not intended to be construed as limiting the scope of the present invention.

Example 1

Scheme 2

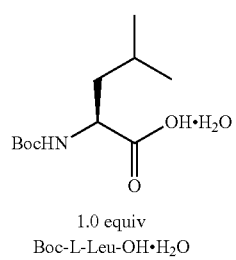

1.0 equiv
Boc-L-Leu-OH·H₂O i. PivCl (1.0 equiv)
  N-methylmorpholine (1.0 equiv)
  IPAc (8 V)
ii. morpholine (1.1 equiv)
   -5 to 20° C.
iii. wash with 1M H₂SO₄,
    1M NaOH, and water
iv. solvent swap to THF/heptane

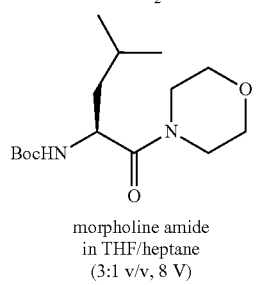

morpholine amide
in THF/heptane
(3:1 v/v, 8 V)

i. Mg turnings (2.2 equiv)
ii. iPrMgCl (2.0M in THF,
    1.0 equiv), 0° C.
iii. 2-bromopropene (1.8 equiv)
    portionwise at 35° C.
iv. quench with aq. citric acid
    and heptane
v. wash with water
vi. silica pad
vii. concentrate to an oil

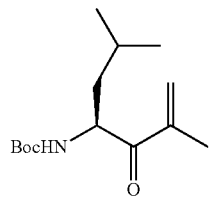

Intermediate 1
75% yield (two steps)

Synthesis of (S)-tert-butyl (2,6-dimethyl-3-oxohept-1-en-4-yl)carbamate (Intermediate 1)

Step 1: (S)-tert-butyl (4-methyl-1-morpholino-1-oxopentan-2-yl)carbamate

The starting material (S)-2-(tert-butoxycarbony)amino)-4-methylpentanoic acid monohydrate (Boc-Leu-OH.H₂O; 1.0 equivalent) was charged to a reaction vessel. Isopropyl acetate (8 ml per gm of Boc-Leu-OH.H₂O) was added to the vessel and the mixture was stirred at 15° C. to 25° C. to dissolve Boc-Leu-OH.H₂O. The solution was then cooled to −10° C. to −5° C. Pivalic acid (1.0 eq) was added to the solution over 5-30 minutes while maintaining the solution temperature between −10° C. and 0° C. The mixture was stirred for 20-40 minutes. The mixture was cooled to −10° C. to −5° C. and morpholine (1.1 eqs) was added over 10-30 minutes while maintaining the reaction temperature between −10° C. and 0° C. The mixture was stirred at −5° C. to 0° C. for 30-60 minutes then warmed to 15-25° C. A 1 molar solution of H₂SO₄ (0.8 ml per gm boc-Leu-OH, H₂O; 0.2 eq) was then added over 5-30 minutes while maintaining the temperature between 15-30° C. The mixture was stirred for 15-30 minutes, then the aqueous layer is removed. A 1 molar solution of NaOH (4.4 ml per gm boc-Leu-OH.H₂O; 1.1 eq) was added over 5-30 minutes while maintaining the temperature between 15-30° C. The mixture was stirred for 15-30 minutes, then the aqueous layer is removed. Water (5 ml per gm boc-Leu-OH.H₂O) was added over 5-30 minutes while maintaining the temperature between 15-30° C. The mixture was stirred for 15-30 minutes, then the aqueous layer is removed. The isopropylacetate solution was concentrated under vacuum to 3 to 4 volumes, then heptane (4 mL per gm) was added over 5-15 minutes. The mixture was concentrated under vacuum to 3 to 4 volumes, then heptane (4 mL per gm) was added over 5-15 minutes. The mixture was again concentrated under vacuum to 3 to 4 volumes, then heptane (4 mL per gm) was added over 5-15 minutes. This azeotropic step was repeated until <1% isopropyl acetate remains (by GC analysis). The contents were then distilled to about 1 volume of heptane, then charged with THF (3 mL per gm) and stored at 15-25° C. or used in step 2.

Yield: 90% (based on HPLC assay)

Step 2: (S)-tert-butyl (2,6-dimethyl-3-oxohept-1-en-4-yl)carbamate (Intermediate 1)

(S)-tert-butyl (4-methyl-1-morpholino-oxopentan-2-yl) carbamate (1.0 eq) dissolved in THF (3 mL per gm) and heptane (1 mL per gm) was charged to a reaction vessel that was flushed with nitrogen gas. THF (3 mL per gm) and heptanes (1 mL per gm) were added to bring the solution to a total of 8 mL per gm morpholino starting material.

Magnesium powder (2.2 eqs; Sigma Aldrich or Alfa Aesar) was added and the solution was cooled −10° C. to −5° C. i-PrMgCl (2.0M solution in THF; 1.0 eq) was added to the reaction while maintaining the temperature between −10° C. and 0° C. The solution was then warmed to 35° C. and 2-bromopropene (0.15 eq) was added. The temperature was monitored to observe initiation of the Grignard reaction which results in about a 5-10° c. exotherm. Once the temperature dropped to <40° C., the remaining 2-bromopropene (1.56 eq, 1.8 eq in total) was added at a rate to maintain the temperature below 42° C. After complete addition of bromide, the solution was stirred at 30-35° C. for 3 hours, or until >99% conversion was observed by HPLC. The solution was cooled to ambient temperature, then added to a reaction vessel containing citric acid (8 mL per gm of morpholino starting material, 30% w/w in H$_2$O) and heptane (2 mL per gm) cooled to −10° C. to −5° C., while maintaining the temperature between −10° C. to −5° C. During the quench it was important to keep the unquenched reaction solution stirring, as the stagnant solution could solidify and cause clogging of the pump. The quenched solution was warmed to ambient temperature and stirred for 15-30 minutes and the aqueous layer was removed. Water (5 mL per gm) was added over 5-30 minutes while maintaining the temperature at 15-30° C. The mixture was stirred for 15-30 minutes and the aqueous layer was removed. SiO$_2$ (2 gm/gm, 60 um 70-230 mesh) was added to the solution and the slurry was stirred for 15-30 minutes. The slurry was then filtered through a wet pad of SiO$_2$ (2 gm SiO$_2$/gm of morpholino starting material), washed with 2% IPAc in heptanes (10 mL per gm). The solution was concentrated to afford Intermediate 1, which was either stored for later use or immediately used in the next step. Yield: 83% (based on HPLC assay). This method of generating the morpholino intermediate above is efficient as it reduced the volume of previous methods from 50 V to 25 V and tedious and time-consuming column chromatography for purification was replaced with a silica gel plug filtration. The product of example 1 was isolated from Boc-L-Leu.monohydrate with an assay yield of 75% over two steps.

Example 2

Scheme 3

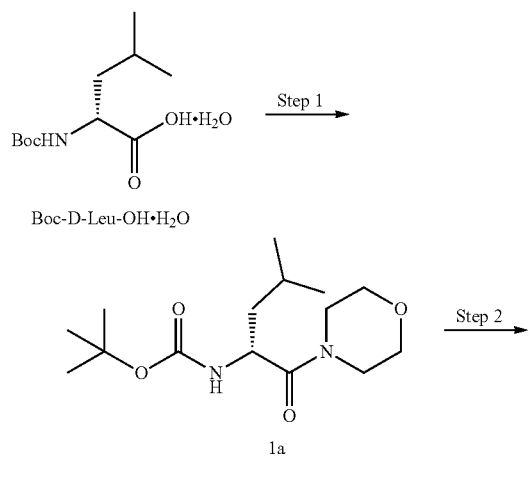

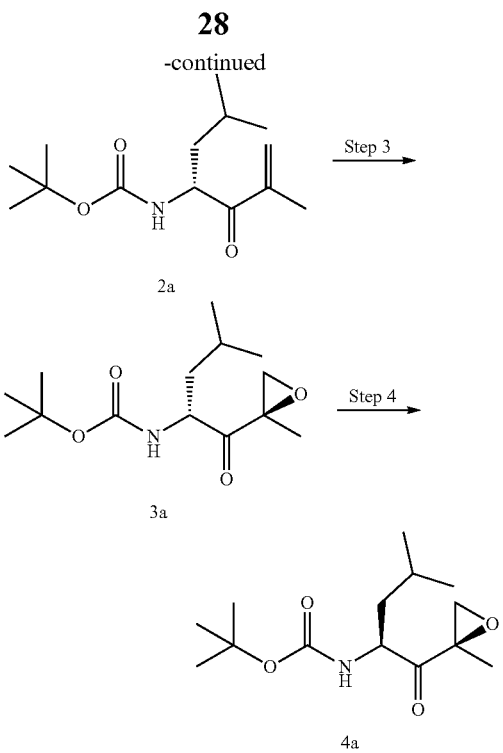

Synthesis of tert-butyl ((S)-4-methyl-1-((R)-2-methyloxiran-2-yl)-1-oxopentan-2-yl)carbamate (Also Referred to as Compound A Herein)

Step 1: Synthesis of (R)-tert-butyl (4-methyl-1-morpholino-1-oxopentan-2-yl)carbamate A solution of (R)-2-((tert-butoxycarbonyl)amino)-4-methylpentanoic acid monohydrate (1.0 equiv) in THF (2.5 mL/gm) was concentrated under vacuum to remove residual water. Methyl tert-butyl ether (5 mL/gm) was added and the solution was cooled to 0° C. A slurry of 1,1′-carbonyldiimidazole (1.2 equiv) in methyl tert-butyl ether (3 mL/gm) was added to the reaction at a rate to maintain the reaction temperature≤5° C. and the reaction mixture was stirred at 0° C. for 1 h. To the cooled reaction mixture was added morpholine (1.5 equiv) at a rate to maintain reaction temperature≤10° C. and the reaction mixture was stirred for 1 h at 0° C. A 1 M aqueous solution of hydrogen chloride (3.5 mL/gm) was added and the biphasic mixture was warmed to 20° C. and stirred for 15 min. The layers were allowed to separate and the bottom aqueous layer was removed. The organic layer was washed sequentially with a 1 M aqueous solution of hydrogen chloride (1.5 mL/gm), an 8 wt % aqueous solution of sodium bicarbonate (1 mL/gm), and a saturated aqueous solution of sodium chloride (3 mL/gm). The organic solution containing (R)-tert-butyl (4-methyl-1-morpholino-1-oxopentan-2-yl)carbamate was concentrated under vacuum to remove residual water, reconstituted with methyl tert-butyl ether (5 mL/gm), to provide compound 1a and used in the following step without additional purification. Yield: 99% (based on HPLC assay)

$^1$H NMR (400 MHz CDCl$_3$): 5.26 (d, J=8.9 Hz, 1H), 4.62 (m, 1H), 3.45-3.72 (m, 8H), 1.71 (m, 1H), 1.42 (m, 11H), 0.96 (d, J=6.7 Hz, 3H), 0.92 (d, J=6.5 Hz, 3H)

HRMS (ESI-TOF) m/z calcd for C$_{15}$H$_{29}$N$_2$O$_4$ (M+H)$^+$ 301.2127, found 301.2126.

Step 2: Synthesis of (R)-tert-butyl (2,6-dimethyl-3-oxohept-1-en-4-yl)carbamate (2a)

To a reactor flushed with nitrogen gas was charged Mg turnings (2.1 equiv), the solution from step 1 containing (R)-tert-butyl (4-methyl-1-morpholino-1-oxopentan-2-yl) carbamate, and THF (3 mL/gm). The slurry was cooled to 0° C. and isopropenyl magnesium chloride (1.9 M solution in THF, 0.9 eq) was added at a rate to maintain the reaction temperature≤10° C. The reaction mixture was then warmed to 40° C. and 2-bromopropene (0.2 eq) was added to initiate the Grignard formation. Once the initial exotherm (~5-10° C.) had subsided, 2-bromopropene (1.8 equiv) was added portionwise (0.3 eq portions) to maintain the reaction temperature≤50° C. The reaction mixture was stirred for >2 h at 40° C., cooled to 20° C., and then added to a separate pre-cooled (0° C.) vessel containing a 25 wt % aqueous solution of citric acid (9 mL/gm) and methyl tert-butyl ether (5 mL/gm) at a rate to maintain the reaction temperature≤5° C. The biphasic mixture was warmed to 20° C., the layers allowed to separate, and the lower aqueous layer removed. The organic layer was washed sequentially with water (5 mL/gm), an 8 wt % aqueous solution of sodium bicarbonate (5 mL/gm), and a saturated aqueous solution of sodium chloride (5 mL/gm). The organic solution containing (R)-tert-butyl (2,6-dimethyl-3-oxohept-1-en-4-yl)carbamate was concentrated under vacuum, reconstituted with acetonitrile (10 mL/gm) to provide compound 2a, which was used in the next step without additional purification. Yield: 85% (based on HPLC assay)

$^1$H NMR (400 MHz CDCl$_3$): $^1$H NMR (400 MHz, CDCl$_3$) 6.09 (s, 1H), 5.89 (s, 1H), 5.10 (m, 2H), 1.91 (s, 3H), 1.74 (m, 1H), 1.49 (m, 1H), 1.44 (s, 9H), 1.34 (m, 1H), 1.01 (d, J=6.5 Hz, 3H), 0.92 (d, J=6.6 Hz, 3H)

HRMS (ESI-TOF) m/z calcd for C$_{14}$H$_{25}$NNaO$_3$ (M+Na)$^+$ 278.1732, found 278.1731.

Step 3: Synthesis of tert-butyl ((R)-4-methyl-1-((R)-2-methyloxiran-2-yl)-1-oxopentan-2-yl)carbamate (3a)

To a reactor containing the solution of (R)-tert-butyl (2,6-dimethyl-3-oxohept-1-en-4-yl)carbamate (1.0 eq) in ACN (10 mL/gm) from Step 2 was added the mangenese catalyst (0.0004 eq) and HOAc (5.0 eq). The reaction mixture was cooled to −20° C. and a 50 wt % aqueous solution of hydrogen peroxide (2.0 eq) was added at a rate to maintain reaction temperature≤−10° C. The reaction mixture was stirred at −20° C. for 2 h, warmed to 5° C., and quenched with a 25 wt % aqueous solution of sodium bisulfite (3.7 equiv). The biphasic mixture was warmed to 20° C., the layers allowed to separate, and the lower aqueous layer removed. The organic solution was concentrated under vacuum and reconstituted with isopropanol (4 mL/gm). Water (6 mL/gm) was added over 2 h and the resultant white slurry was cooled to 5° C. and filtered to provide tert-butyl ((R)-4-methyl-1-((R)-2-methyloxiran-2-yl)-1-oxopentan-2-yl)carbamate (compound 3a) as a white crystalline solid (77% yield).

$^1$H NMR (400 MHz CDCl$_3$): 4.88 (in, $^1$H), 4.58 (m, 1H), 3.04 (d, J=5.1 Hz, 1H), 2.86 (d, J=5.1 Hz, 1H), 1.71 (m, 1H), 1.56 (s, 3H), 1.44 (s, 9H), 1.36 (m, 2H), 0.98 (d, J=6.4 Hz, 3H), 0.93 (d, J=6.6 Hz, 3H)

HRMS (ESI-TOF) m/z calcd for C$_{14}$H$_{25}$NNaO$_4$ (M+Na)$^+$ 294.1681, found 294.1680.

Step 4: Synthesis of tert-butyl ((S)-4-methyl-1-((R)-2-methyloxiran-2-yl)-1-oxopentan-2-yl)carbamate (4a)

To a 20° C. solution of tert-butyl ((R)-4-methyl-1-((R)-2-methyloxiran-2-yl)-1-oxopentan-2-yl)carbamate (1.0 eq) in methyl tert-butyl ether (10 mL/gm) was charged 1,8-diazabicyclo[5.4.0]undec-7-ene (0.20 eq). The reaction mixture was allowed to stir at 20° C. for 12 h and then washed with a 5 wt % aqueous solution of sodium bisulfate (0.50 eq). The layers were allowed to separate and the bottom aqueous layer removed. The organic layer was washed with water (5 mL/gm), concentrated under vacuum, and reconstituted with N-methylpyrrolidinone (5 mL/gm). Simultaneous addition of the organic solution and water (5 mL/gm) to a pre-cooled (5° C.) slurry of tert-butyl ((S)-4-methyl-1-((R)-2-methyloxiran-2-yl)-1-oxopentan-2-yl)carbamate (0.05 equiv) in N-methylpyrrolidinone/water (1:1 v/v, 5 mL/gm) generated a slurry, which was filtered to provide compound 4a, tert-butyl ((S)-4-methyl-1-((R)-2-methyloxiran-2-yl)-1-oxopentan-2-yl)carbamate, as a white crystalline solid (84% yield).

$^1$H NMR (400 MHz CDCl$_3$): 4.86 (d, J=8.5 Hz, 1H), 4.31 (m, 1H), 3.29 (d, J=4.9 Hz, 1H), 2.88 (d, J=5.0 Hz, 1H), 1.72 (m, 1H), 1.51 (s, 3H), 1.48 (m, 1H), 1.41 (s, 9H), 1.17 (m, 1H), 0.96 (d, J=6.5 Hz, 3H), 0.93 (d, J=6.6 Hz, 3H)

HRMS (ESI-TOF) m/z calcd for C$_{14}$H$_{25}$NNaO$_4$ (M+Na)$^+$ 294.1681, found 294.1681.

The morpholine amide step 1 may be accomplished using a variety of acid coupling reagents, each of which is referred to herein an "acid activating agent." The term "acid activating agent" is intended to refer to an agent that is capable of converting the hydroxyl group of a carboxylic acid functional group to a labile moiety susceptible to displacement upon nucleophilic attack. For instance, an acid activating group that can convert the hydroxyl group of the carboxylic acid moiety of Boc-D-leucine-OH to a group that is easily displaced by the nucleophilic morpholine nitrogen, thereby affording the step 1 morpholine amide product. Similarly, the "activated" carboxylic acid functional group can be displaced by CH$_3$NHOCH$_3$ to form the corresponding weinreb amide (See compound 9 herein). Examples of classes and types of acid activating reagents include, without limitation, (a) formation of an acid chloride by use of thionyl chloride, oxalyl chloride, phosphorus oxychloride, or a vilsmeier reagent; (b) formation of an anhydride by use of carboxylix/carbonic acid anhydrides, a sulfonate mixed anhydrides such as methane sulfonyl chloride (MsCl) or p-toluene sulfonyl chloride (TsCl); a phosphorus based mixed anhydride such as n-propanephosphonic acid anhydride (T3P) or ethylmethylphosphonic anhydride; (c) formation of an activated ester moiety by use of a carbodiimide such as dicyclohexylcarbodiimide (DCC), N,N-diisopropylcarbodiimide (DIC) or 1-ethyl-3-(3'-dimethylaminopropyl) carbodiimide (ECD), or HOBt (1-hydroxybenzotriazole), HOAt (1-hydroxy-7-azabenzotriazole); (d) formation of a guanidinium or uronium salts such as with N,N,N',N'-tetramethyl-O-(1H-benzotriazol-1-yl)uronium hexafluorophosphate (HBTU), N-[(dimethylamino)-1H-1,2,3-triazolo [4,5-b]pyridine-1-yl-methylene]-N-methylmethanaminium hexafluorophosphate (HATU), N-[(1H-benzotriazol-1-yl) (dimethylamino)methylene]-N-methylmethanaminium tetrafluoroborate-N-oxide (TBTU), 2-(2-oxo-1(2H)-pyridyl-11,3,3-tetramethyluronium tetrafluoroborate (TPTU) and O-[(cyano(ehtoxycarbony)-methyleneamino]-N,N,N',N'-tetramethyluronium terafluoroborate (TOTU); (e) formation of an anhydride using 1,1'-carbonyldiimidazole (CDI); or (f)

formation of a phosphonium salt using an agent such as benzotriazol-1-yloxy)tris-(dimethylamino)phosphonium hexafluorophosphate (Castro's reagent or BOP) or (benzotriazol-1-yloxy)tris(pyrrolidine)-phosphonium hexafluorophosphate (PyBOP). These and other acid activating agents are described in more detail in Org Process Res. Dev., 20, 140-177, 2016.

The method of Example 2 is novel as it begins with amine-protected-D-leucine as the starting material. Example 2 also presents the advantage of reducing the volume of the Grignard step from 50 V to 25 V. This significantly improves scalability and throughput, and protects the environment by reducing generated solvent waste. Example 2 also completely eliminates tedious and time-consuming column chromatography operation in both steps 2 and 3. The impurities that would have been removed via chromatography can now be removed via crystallization of the step 3 and step 4 products. Finally, example 2 utilizes mild reaction conditions thereby mitigating risks of epimerization.

Note that excess water may be removed from the Boc-D-Leu-OH.monohydrate by azeotropic distillation in THF (2×2.5 vol). However, where the CDI molar equivalents is higher, azeotropic distillation of the water may not be needed. The final water level of <1000 ppm was achieved for the acid activation step. Various acid activating agents for Boc-D-Leu-OH were used (Piv-Cl, CDI, T$_3$P, DIC/oxyma, cyanuric chloride and diphenylphosphonic chloride). Use of T3P resulted in an emulsion in the aqueous work-up contributing to additional time for separation. Use of diphenyl phosphonic chloride resulted in a high yielding reaction, but containing a difficult to remove by-product. Use of DIC resulted in an 88% yield for step 1 after column chromatography, by also was found to contain a by-product which needed to be separated. Use of Piv-chloride, run at about 0° C. also resulted in high yields (about 95%) and contained a piv-amide impurity necessitating additional purification. CDI was elected as the activating agent of choice as it provided a clean reaction profile with a high yield in the shortest reaction time. It was found that the temperature of the reaction when using CDI was important and meaningfully affected the product yield. For instance, it was discovered that the best results were obtained when the reaction was conducted at a temperature of at or below 20° C. In one aspect of the invention, the invention provides the morpholine amide step 1 to be conducted at a temperature of at or below 20° C. In another aspect of the invention, the invention provides the morpholine amide step 1 to be conducted at a temperature of at or below 10° C. In another aspect, the invention provides the methods described herein wherein the morpholine amide step 1 comprises formation of the activated acid with CDI at a temperature of at or below 5° C., and the morpholine amide formation portion of the reaction to be conducted at or below 10° C. The reaction step 1 to form the morpholine-amide was performed in a variety of solvents including THF, Me-THF, toluene and MTBE. In one aspect of the invention, the solvent MTBE (10 V) was selected for this step. IN another aspect of the invention, the solvent MeTHF was used. Among the solvents that were evaluated using dynochem modelling software for a straightfoward solvent swap, methyl tert-butyl ether (MTBE) was identified as a choice solvent for exchange to ACN due to the minimal distillation operations required. Therefore, optimization of the two-step sequence was carried out using MTBE or a combination of MTBE and THF to improve solubility. Additionally, while solvents other than ACN may be used in the epoxidation step 3, ACN was found to be the solvent of choice for the given conditions and providing an optimal yield.

Though the CDI may be used in an amount ranging from about 1.0 equivalent to about 2.5 eq, the optimal amount of CDI used for activation in step 1 was found to be about 2.0 equivalents. If one were to use less CDI equivalents, such as on ly about 1.2 equivalents of CDI, then one would likely need to azeotropically remove water from the reaction. The optimal activation time was found to be about 3.0 hours. The time may vary depending upon the apparatus set-up used. Certain apparatus set-ups, such as continuous manufacturing set-up may take less time, such as little as 2 minutes. These conditions resulted in a product yield of about 98% (Table 2, entry 1). With a slight excess of CDI, 1.5 equivalents of morpholine was found to be optimal for the coupling reaction. The morpholine-amide adduct was isolated as a crystalline solid and may be used as an MTBE solution as both the yield and purity after work-up were superior (99.0% assay yield, >99.5 LCAP) without any racemization observed under standard conditions. Therefore, the product was telescoped as an MTBE solution and subjected to azeotropic distillation to remove residual water (target<500 ppm).

The Grignard reaction step 2 was found to be optimal when conducted using the morpholine-amide solution in MTBE (5 V). An important challenge in this step from both a product-quality and safety perspective was confirmation of the activation process to form the Grignard reagent in situ and control of this exothermic process. A potential safety issue was the accumulation of 2-bromopropene and delay in initiation/activation of Mg(0) turnings. The latent exotherm generated due to delayed activation could have led to uncontrolled excursion of temperature that may have been difficult to handle in a large-scale manufacturing environment.

THF (3 V) was found to be a suitable co-solvent in this step as it was found to alleviate the generation of solids during the reaction, which solids would have resulted in poor agitation of the reaction mixture. Isopropylmagnesium chloride solution (2M in THF, 0.9 equiv) was used as a sacrificial base to deprotonate the amide and for activation of the Mg turnings (2.1 equiv) prior to addition of 2-bromopropene. The stoichiometry of isopropylmagnesium chloride was important to reduce or eliminate the potential impurity from isopropylmagnesium chloride addition to the morpholine amide. Again, depending upon the apparatus used, one may not need to use isopropylmagnesium chloride at all. This was the case where a continuous manufacturing set-up was used. Both the formation of Grignard (isopropenylmagnesium bromide) and its reaction with morpholine-amide were found to be rapid and efficient by UPLC and react-IR. The bromide was consumed in about 20-30 minutes after each charge of 2-bromopropene and the corresponding product formation was observed by UPLC. React-IR results demonstrated that there was no accumulation of 2-bromopropene and the reaction remained safe throughout the dose-controlled addition process. Based on the data collected during the use-test and scale-up runs, the process achieved conversion ranging from >97% to about 99.7% or practically complete conversion with only about 1.2-2.0 equivalents of 2-bromopropene. About 1.4-1.5 equivalents of 2-bromopropene was discovered to be optimal, resulting in about a 99% conversion for step 2. The impurity profile of the step 2 Grignard was dependent in part ojn the quality of the 2-bromopropene. These impurities were important to monitor to ensure column chromatography could be avoided. The potential impurity in 2-bromopropene is estimated to be polymeric in nature and resulted in stalling of the downstream epoxidation process. Using re-distilled 2-bromopropene (93.3 wt % by qNMR), the resultant Grignard product of step 2 was found to perform well in the following epoxidation step 3.

Appropriate quenching of the Grignard process is important to ensure product quality and to eliminate racemization. A Grignard adduct impurity resulting from double-addition of the Grignard reagent was detected by LCMS at ~2 LCAP during inverse addition of the reaction mixture to a mixture of MTBE (5 V) and 25% citric acid aqueous solution (10 V). An increase in the level of the double-addition by-product (up to 11 LCAP) was observed when quenching the reaction mixture into citric acid solution (in the absence of MTBE) with an associated decrease in product yield by >35%. The excess Grignard could react with product of step 2 that was hydrolyzed after work-up leading to the formation of the impurity. Of note, the impurities of double-addition, morpholine-adduct and dimers could not be detected by HPLC due to their relatively low response factors, but could be detected by LCMS and TLC (EtOAc/heptane 1:4, Nihydrin). Thus, it is important to carefully control the amount of Grignard reagents used and to carefully quench the reaction upon completion. Racemization of step 2 product was not observed during the course of optimization of the Grignard process or during the inverse quenching step. The concentrated product with BHT was stable at ambient temperature for one month; BHT in this sample originated from the solvent (250 ppm in stabilized THF) used in the Grignard process. The solution containing the product of step 2 in 2-10 V of ACN or MTBE was stable at room temperature or 5° C. for at least 4 days or 18 hours at 35° C., which was required to optimize the solvent switch to ACN for the step 3 epoxidation.

The improved process of steps 1 and 2 described herein was demonstrated starting from about 1.93 kg boc-D-leucine hydrate and found to be successfully scalable and robust with good solution assay yield (83%) and acceptable product quality (96.7% LCAP and 100% chiral purity) for the subsequent epoxidation step. The Grignard reaction of step 2 can be controlled by addition rate of 2-bromopropene and the total reaction volumes maintained below 25 V, while eliminating the need for column chromatography purification and mitigating racemization risk of the resulting products.

Example 3: Synthesis of (S)-4-methyl-1-((R)-2-methyloxiran-2-yl)-1-oxopentan-2-aminium 2,2,2-trifluoroacetate

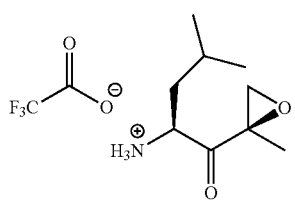

To a cooled (0° C.) solution of tert-butyl ((S)-4-methyl-1-((R)-2-methyloxiran-2-yl)-1-oxopentan-2-yl)carbamate (1.0 equiv) in DCM (3 ml/g) was added TFA (5.0 equiv). The reaction mixture was allowed to warm to 20° C. and aged for 4 h. To the solution was added methyl tert-butyl ether (6.6 ml/g) and then n-heptane (13.3 ml/g). The resultant slurry was cooled to 0° C. and then filtered to afford (S)-4-methyl-1-((R)-2-methyloxiran-2-yl)-1-oxopentan-2-aminium 2,2,2-trifluoroacetate as a white crystalline solid (88% yield)

$^1$H NMR (400 MHz, CDCl$_3$) 8.20 (bs, 3H), 4.05 (dd, J=9.7, 3.2 Hz, 1H), 3.13 (d, J=4.4 Hz, 1H), 2.95 (4.5 Hz, 1H), 1.85 (m, 1H), 1.71 (m, 1H), 1.57 (m, 4H), 1.00 (dd, J=6.5, 2.4 Hz, 6H) HRMS (ESI-TOF) m/z calcd for C$_9$H$_{18}$NO$_2$ (M+H)$^+$ 172.1338, found 172.1333.

The present invention provides methods of making an important intermediate, compound 5, useful for the manufacture of carfilzomib. For example, the invention provides a cost of goods (COG) for synthesis of compound 5 as a TFA salt, by methods of the invention, of about USD $5,975/kg of the TFA salt of compound 5 with an overall yield of about 50% and an E-factor of 304. In contrast, the method taught in PCT publication WO2009045497 results in a COG of about USD$53,124 per kg of the TFA slat of compound 5 with an overall yield of about 14% and an E-factor of 2639. Further, the process of WO2009045497 requires laborious and costly column chromatography, thereby resulting in the poor throughput efficiency and high COG exhibited.

Example 4: Synthesis of Manganese Catalyst Used in the Invention

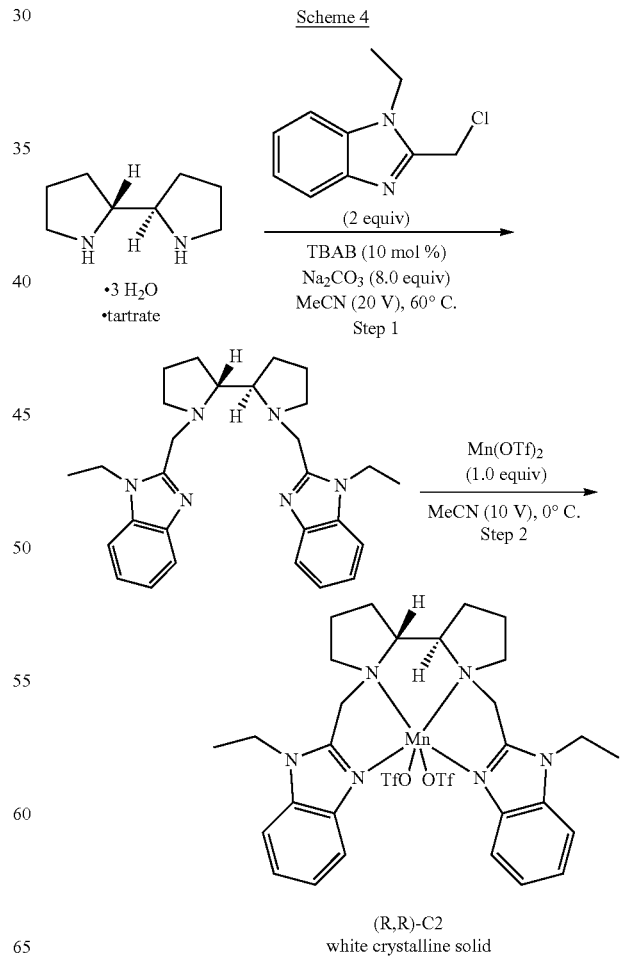

Step 1: Synthesis of (2R,2'R)-1,1'-bis((1-ethyl-1H-benzo[d]imidazol-2-yl)methyl)-2,2'-bipyrrolidine (Catalyst Ligand)

To a solution (20° C.) of (2R,2'R)-2,2'-bipyrrolidine L-tartrate trihydrate (1.0 equiv, commercially available) in ACN (15 ml/g) was added 2-(chloromethyl)-1-ethyl-1H-benzo[d]imidazole (2.0 equiv), tetrabutylammonium bromide (0.10 equiv) and sodium carbonate (8.0 equiv) and then the reaction mixture was heated to 55° C. After aging for 20 h at 55° C., the reaction mixture was cooled to 20° C., filtered through a pad of celite and concentrated under vacuum. The resulting oil was reconstituted with DCM (20 ml/g) and washed with a 1 M aqueous solution of NaOH (20 ml/g). The aqueous layer was extracted with DCM (2×10 ml/g) and the combined organic layers were washed with a saturated aqueous solution of sodium bicarbonate (10 ml/g), and a saturated aqueous solution of NaCl (10 mL/g). The organic layer was dried over sodium sulfate and concentrated under vacuum to provide (2R,2'R)-1,1'-bis((1-ethyl-1H-benzo[d]imidazol-2-yl)methyl)-2,2'-bipyrrolidine as an oil with >95% mass recovery. The crude oil was used in the following step without additional purification.

$^1$H NMR (400 MHz, (CD$_3$)$_2$SO)) 7.54 (m, 4H), 7.18 (m, 4H), 4.32 (m, 6H), 3.53 (m, 2H), 2.86 (m, 2H), 2.63 (m, 2H), 2.21 (m, 2H), 1.86-1.45 (m, 8H), 1.33 (t, J=7.1 Hz, 6H)

HRMS (ESI-TOF) m/z calcd for C$_{29}$H$_{37}$N$_6$ (M+H)$^+$ 457.3080, found 457.3086.

Step 2: Synthesis of C2 Manganese Catalyst

To a solution (20° C.) of (2R,2'R)-1,1'-bis((1-ethyl-1H-benzo[d]imidazol-2-yl)methyl)-2,2'-bipyrrolidine (1.0 equiv) in ACN (5 ml/g) was added a pre-made solution of manganese bis(trifluoromethanesulfonate) (1.0 equiv) in ACN (5 ml/g). The resultant slurry was allowed to age for 20 h at 20° C., cooled to 0° C., and then filtered. The filter cake was washed with ACN (2×2 ml/g) to generate the Mn-complex as a white crystalline solid (35% yield).

HRMS (ESI-TOF) m/z calcd for C$_{29}$H$_{36}$F$_3$MnN$_6$O$_3$S (M-OTf)$^+$ 660.1902, found 660.1913.

Multi-gram quantities of the ligand were prepared in-house; complexation with Mn(OTf)$_2$ provided a crystalline, air-stable Mn-catalyst complex that could be isolated from ACN. The process to prepare this catalyst works on a manufacture grade scale and successfully provided 44 g of the Mn-catalyst, which was an amount sufficient to prepare about 20 kg of compound 4a using the methods of the present invention.

Discovery of Mn-Catalyst for the Asymmetric Epoxidation (Step 3 of Example 2)

The published literature epoxidation methods to prepare compound 2a of Example 2 used protocols that lacked compatibility with the enone substitution pattern of compound 2a. First, the electron-deficient nature of the olefin in 2a requires a nucleophilic epoxidation method. This precludes the more commonly chosen asymmetric epoxidation methods such as, Jacobsen, Sharpless and Shi epoxidation. In addition, the steric bulk surrounding the ketone of compound 2a presents a challenge to iminium ion catalysis, which has proven to be a promising approach for the asymmetric epoxidation of enals (See for example Bonzic, B. P et al, *Org Lett.* 2010, 12, 5434-5437). Lewis-acid catalysis (See Hinch, M. et al. *J. Mol. Catal.* 2006, 251, 123-128; Nemoto, T. et al. *J. Am. Chem. Soc.* 2001, 123, 2725-2732) and thiourea-based activation methods also proved challenging for this reason. Phase-transfer catalysis protocols (See, for example: Lifchits, O. et al. *J. Am. Chem. Soc.* 2013, 135, 6677-6693) suffered from poor conversions or epimerization of the labile amino-acid side chain.

A manganese-catalyzed asymmetric epoxidation was described in the literature (See Wang, B.; et al. *Chem. Eur. J.* 2012, 18, 6750-6753). The method in Wang utilizes a non-commercial Mn-catalyst (C1) in the presence of H$_2$O$_2$ and AcOH. When the Wang method was applied to intermediate compound 1 (See Example 1; also shown below in Scheme 5 below), to prepare compound 4a (Example 2), it resulted in providing the epoxide in good yield with good diastereoselectivity favoring the undesired product.

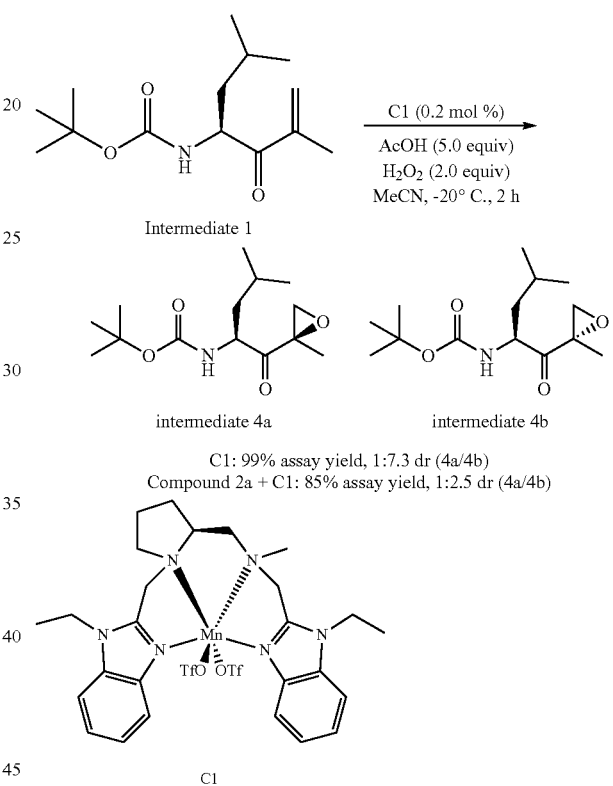

Scheme 5

Use of the Wang manganese catalyst (C1) on the D-enantiomer (compound 2a of Example 2) resulted in a diminished yield and decreased selectivity still favoring the undesired epoxide diasteromer 4b. This data indicated that the Wang manganese catalyst C1 and the enone derived from Boc-L-Leucine could not be used to form the desired epoxide product 4a in high yields. Instead, an improved manganese catalyst and the enone derived from the unnatural Boc-D-Leucine was required for a scalable process. To this end, the Applicants' invention further provides herein a managanese catalyst capable of supporting the efficient, improved epoxidation yields of compound 2a and amenable to larger, manufacture level scale.

Extensive optimization of the ligand, metal, acid, additive, oxidant, temperature, and solvent were not successful in identifying reaction conditions suitable for reversing the diastereoselectivity of the epoxidation reaction. Control experiments demonstrated the unpredictable nature of each reagent in the reaction system, i.e., each reagent was important for the desired conversion and stereoselectivity. Of the various manganese catalysts discovered and tested, C2 (see scheme 4) was found to be the most efficient catalyst for the transformation of compound 2a to compound 3a (in scheme 3) in terms of catalyst loading (0.04 mol %), reaction conversion (>99.5%), and diastereoselectivity (affording about a 10:1 stereoisomeric ratio favoring the desired product 3a). More specifically, the Mn catalyst of the present invention is capable of converting compound 2a to compound 3a in a diastereoselectivity of about 90-95% favoring the desired product (3a). The manganese catalyst structure, and in particular, the precise ligand structure was found to have a significant impact on the diastereoselectivity of the epoxidation step.

Despite the preference for this Mn-catalyzed epoxidation process to produce the undesired epoxide diastereomer, efforts on epimerization of the amino-acid side chain surprisingly revealed a thermodynamic preference for the desired stereochemistry of compound 4a (Example 2). Thus, it was unexpectedly found that the stereoselective synthesis of compound 3a from the D-enantiomer of compound 2a with the Mn-catalyzed epoxidation, followed by a thermodynamically-favored epimerization step, provided an expedient route to the desired product 4a. To this end, the present invention addresses some of the major challenges associated with the commercial manufacture of compound 4a including without limitation, safety, throughput efficiency, overall yield, and cost of goods.

Importantly, the intermediate synthesis of compound 3a allowed for the development of a crystallization process capable of purging upstream impurities and eliminating the requirement for column chromatography at step 1 or 2. The crystallization of compound 4a as a method of purifying compound 4a presented challenges due to its low-melting point (41° C.) and high solubility in most all organic solvents. For example, it was found that the solubility of compound 4a in n-hexane at −20° C. is about 34 mg/mL. Conversely, compound 3a melts at 78° C. and has demonstrated an improved solubility profile allowing for greater flexibility in developing isolation conditions. Heptane and IPA/water were found to be two potential solvent systems for the isolation of compound 3a. Alternatively, a ternary system of three (3) solvents, such as acetonitrile/water/acetic acid will also work to isolate compound 3a. Further, the epoxidation step 3 in scheme 3 using the Mn-y76t catalyst of the present invention followed by crystallization with IPA/water worked well to not only to purge the diasteromer impurity but also to purge upstream process impurities. Finally, the epoxidation chemistry of step 3 in scheme 3 unexpectedly demonstrated excellent consistency across a wide range of compound 2a of varied quality and purity thus demonstrating a robust process.

The foregoing is merely illustrative of the invention and is not intended to limit the invention to the disclosed uses. Variations and changes, which are routine to one skilled in the art, are intended to be within the scope and nature of the invention, which are defined in the appended claims. All mentioned references, patents, applications and publications, are hereby incorporated by reference in their entirety, as if here written.

What is claimed is:

1. A method of making compound 5

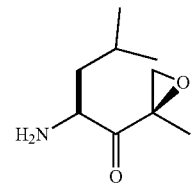

or a pharmaceutically acceptable salt thereof, the method comprising steps 1-5 according to scheme

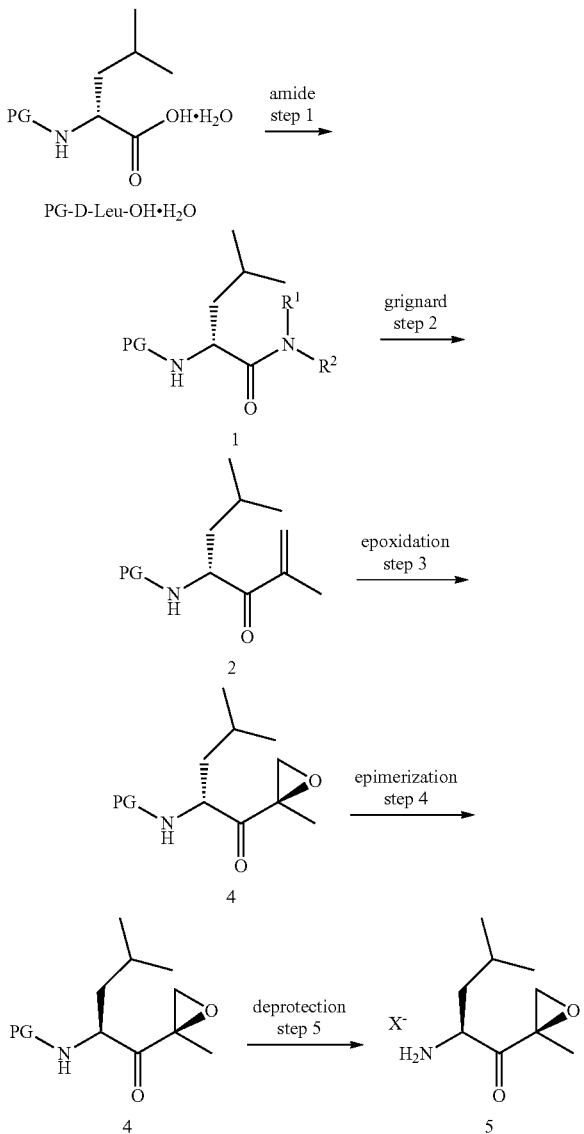

wherein

PG is a protecting group selected from t-butoxycarbonyl (Boc) and carboxybenzyl (cbz);

R¹ is CH₃ and R² is —OCH₃ or R¹ and R² taken together with the nitrogen atom to which they are attached form a morpholine ring;

X⁻ is absent or X⁻ is an addition salt anion selected from trifluoroacetic acid (TFA), Cl, Br, I and mesylate;

the amide step 1 comprises use of an acid activating agent and a basic amine selected from (CH₃)NH(OCH₃) and morpholine;

the Grignard step 2 comprises use of isopropyl magnesium chloride, Mg and 2-bromopropene or isopropenylmagnesium bromide;

the epoxidation step 3 comprises use of an oxidizing agent and a manganese catalyst;

the epimerization step 4 comprises the use of a base; and the deprotection step 5 comprises use of a catalyst or an acid.

2. The method of claim 1 wherein PG is t-butoxycarbonyl (Boc).

3. The method of claim 1 wherein PG is carboxybenzyl (cbz).

4. The method of claim 1 wherein amide step 1 comprises use of morpholine and an acid activating agent selected from 1,1'-carbonyldiimidazole (CDI), dicyclohexylcarbodiimide (DCC), N-[(1H-benzotriazol-1-yl)(dimethylamino)methylene]-N-methylmethanaminium tetrafluoroborate-N-oxide (TBTU), N-[(dimethylamino)-1H-1,2,3-triazolo[4,5-b]pyridine-1-yl-methylene]-N-methylmethanaminium hexafluorophosphate (HATU), (benzotriazol-1-yloxy)tris(pyrrolidine)-phosphonium hexafluorophosphate (PyBOP), O-(6-chloro-1H-benzotriazol-1-yl)-N,N,N',N'-tetramethyluronium tetrafluoroborate (TCTU), 1-ethyl-3-(3-dimethylaminopropyl)carbodiimide (EDCI), pivaloyl chloride, isobutylchloroformate, propylphosphnic anhydride, triphenylphosphine and N,N-diisopropylcarbodiimide.

5. The method of claim 4 wherein the acid activating agent used in the amide step 1 is 1,1'-carbonyldiimidazole (CDI).

6. The method of claim 1 wherein the Grignard step 2 comprises use of isopropyl magnesiumchloride, Mg and 2-bromopropene.

7. The method of claim 1 wherein the oxidizing agent used in the epoxidation step 3 is selected from hydrogen peroxide (H₂O₂), peracetic acid, t-BuOOH and PhIO.

8. The method of claim 7 wherein the oxidizing agent used in the epoxidation step 3 is hydrogen peroxide.

9. The method of claim 1 wherein manganese catalyst used in the epoxidation step 3 has a structure of

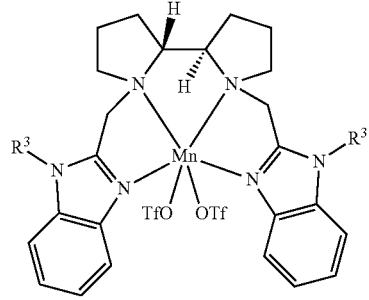

wherein each R³, independently, is methyl or ethyl and TfO is trifluoromethanesulfonate.

10. The method of claim 9 wherein manganese catalyst used in the epoxidation step 3 has a structure of

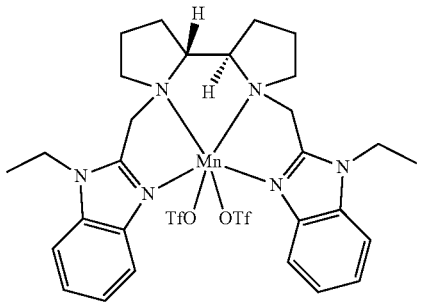

wherein TfO is trifluoromethanesulfonate.

11. The method of claim 1 wherein the base used in the epimerization step 4 is selected from 1,8-Diazabicyclo[5.4.0]undec-7-ene (DBU), triazabicyclodecene (TBD), pyrrolidine, potassium carbonate and sodium hydroxide.

12. The method of claim 11 wherein the base used in the epimerization step 4 is 1,8-Diazabicyclo[5.4.0]undec-7-ene (DBU).

13. The method of claim 11 wherein the base used in the epimerization step 4 is triazabicyclodecene (TBD).

14. The method of claim 1 further comprising a solvent swap involving a switch to an alcohol solvent or a basic solvent.

15. The method of claim 1 further comprising a solvent swap involving a switch to methanol, isopropanol or N-methylpyrrolidinone.

16. A method of making compound 4a

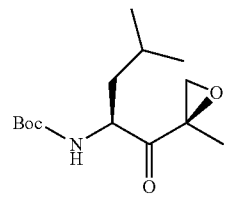

the method comprising steps 1-4 according to scheme 1-a

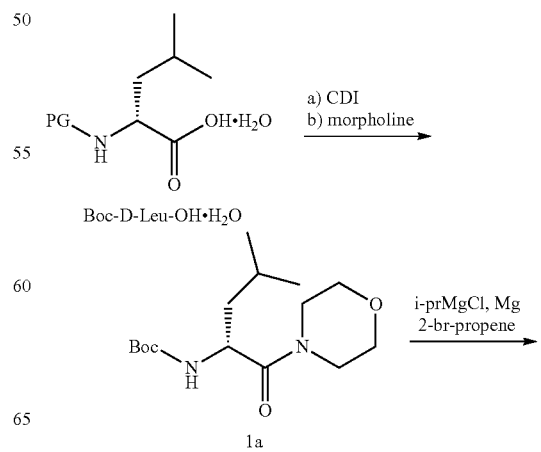

41

-continued

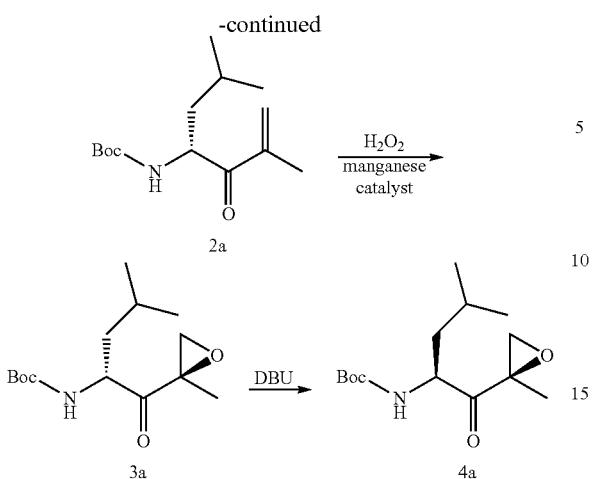

wherein the manganese catalyst has a structure of

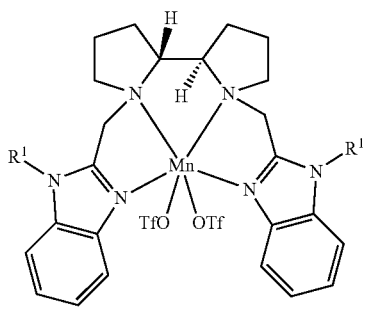

wherein R¹ is methyl or ethyl; TfO is trifluoromethanesulfonate; CDI is 1,1'-carbonyldiimidazole; and DBU is 1,8-Diazabicyclo[5.4.0]undec-7-ene.

17. The method of claim 16 wherein manganese catalyst has a structure of

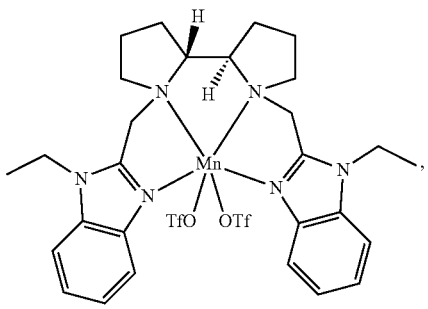

wherein TfO is trifluoromethanesulfonate.

42

18. The method of claim 16, wherein
1,1'-carbonyldiimidazole (CDI) is used in an amount ranging from about 1.0 equivalents to about 2.5 equivalents;
morpholine is used in an amount ranging from about 1.2 equivalents to about 2.0 equivalents;
2-bromopropene is used in an amount ranging from about 1.5 equivalents to about 3.5 equivalents;
hydrogen peroxide ($H_2O_2$) is used in an amount ranging from about 1.5 equivalents to about 3.0 equivalents;
the manganese catalyst is used in an amount ranging from about 0.0002 equivalents to about 0.001 equivalents; and
1,8-Diazabicyclo[5.4.0]undec-7-ene (DBU) is used in an amount ranging from about 0.1 to about 0.5 equivalents.

19. The method of claim 1 wherein the manganese catalyst is used in a amount ranging from about 0.0001 to about 0.002 molar equivalents to the moles of the starting material compound 2.

20. The method of claim 19 wherein the manganese catalyst is used in an amount ranging from about 0.0002 to about 0.001 molar equivalents to the moles of the starting material compound 2.

21. The method of claim 20 wherein the manganese catalyst is used in a amount of about 0.001 molar equivalents to the moles of the starting material 2.

22. The method of claim 14 wherein the solvent swap comprises a switch from acetonitrile (ACN) to methanol between the Grignard step and the epoxidation step.

23. The method of claim 1 further comprising a solvent swap involving a switch to methanol, isopropanol or N-methylpyrrolidinone.

24. The method of claim 16 wherein the manganese catalyst is used in a amount ranging from about 0.0001 to about 0.002 molar equivalents to the moles of the starting material compound 2a.

25. The method of claim 24 wherein the manganese catalyst is used in an amount ranging from about 0.0002 to about 0.001 molar equivalents to the moles of the starting material compound 2a.

26. The method of claim 25 wherein the manganese catalyst is used in an amount of about 0.001 molar equivalents to the moles of the starting material 2a.

27. The method of claim 24 wherein the solvent swap comprises a switch from acetonitrile (ACN) to methanol between the Grignard step and the epoxidation step.

28. The method of claim 24 further comprising a solvent swap involving a switch to methanol, isopropanol or N-methylpyrrolidinone.

* * * * *